(12) United States Patent  (10) Patent No.: US 8,721,657 B2
Kondoh et al.  (45) Date of Patent: May 13, 2014

(54) MEDICAL INSTRUMENT

(75) Inventors: Nobuko Kondoh, Tokyo (JP); Takumi Dejima, Tokyo (JP); Kiyotaka Matsuno, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 108 days.

(21) Appl. No.: 12/103,439

(22) Filed: Apr. 15, 2008

(65) Prior Publication Data

US 2008/0255423 A1  Oct. 16, 2008

Related U.S. Application Data

(63) Continuation-in-part of application No. 11/649,099, filed on Jan. 3, 2007, which is a continuation-in-part of application No. 11/331,938, filed on Jan. 13, 2006, now abandoned.

(51) Int. Cl.
A61F 11/00 (2006.01)
(52) U.S. Cl.
USPC .......................................... 606/108; 600/146
(58) Field of Classification Search
USPC ........... 600/104, 146, 139; 606/184, 108, 167
See application file for complete search history.

(56) References Cited

U.S. PATENT DOCUMENTS

| | | | |
|---|---|---|---|
| 3,320,835 A * | 5/1967 | Flory et al. .......................... 81/54 |
| 3,670,721 A * | 6/1972 | Fukami et al. ................. 600/140 |
| 3,998,216 A | 12/1976 | Hosono | |
| 4,196,736 A | 4/1980 | Watanabe | |
| 4,253,350 A * | 3/1981 | De Tarr ............................ 81/486 |
| 4,362,160 A | 12/1982 | Hiltebrandt | |
| 4,499,895 A * | 2/1985 | Takayama ...................... 600/148 |
| 4,673,073 A * | 6/1987 | Weatherby ....................... 192/35 |
| 4,726,355 A | 2/1988 | Okada | |
| 4,841,888 A | 6/1989 | Mills et al. | |
| 5,041,129 A | 8/1991 | Hayhurst et al. | |
| 5,297,526 A | 3/1994 | Wilk | |
| 5,297,536 A | 3/1994 | Wilk | |
| 5,342,303 A | 8/1994 | Ghaerzadeh | |
| 5,417,699 A | 5/1995 | Klein et al. | |
| 5,437,665 A | 8/1995 | Munro | |

(Continued)

FOREIGN PATENT DOCUMENTS

| | | |
|---|---|---|
| EP | 1 518 507 A1 | 3/2005 |
| EP | 1 602 336 A2 | 12/2005 |
| WO | WO 99/44506 | 9/1999 |
| WO | WO 2006/005075 A2 | 1/2006 |

OTHER PUBLICATIONS

U.S. Office Action dated Mar. 5, 2010 received in related U.S. Appl. No. 11/649,036.

(Continued)

Primary Examiner — Kathleen Holwerda
Assistant Examiner — Sarah Simpson
(74) Attorney, Agent, or Firm — Scully, Scott, Murphy & Presser, P.C.

(57) ABSTRACT

A medical instrument for performing a medical procedure within a body cavity includes: an insertion part which is inserted into the body cavity and has a bending part capable of bending in a predetermined range; a manipulating part which manipulates the bending part; a wire which connects the bending part with the manipulating part; and a clutch which is provided in the manipulating part and maintains a bending state of the bending part.

4 Claims, 38 Drawing Sheets

(56) References Cited

U.S. PATENT DOCUMENTS

| | | |
|---|---|---|
| 5,458,131 A | 10/1995 | Wilk |
| 5,591,179 A | 1/1997 | Edelstein |
| 5,632,717 A | 5/1997 | Yoon |
| 5,643,293 A | 7/1997 | Kogasaka et al. |
| 5,681,260 A | 10/1997 | Ueda et al. |
| 5,700,273 A | 12/1997 | Buelna et al. |
| 5,792,153 A | 8/1998 | Swain et al. |
| RE36,020 E | 12/1998 | Moore et al. |
| 5,935,107 A | 8/1999 | Taylor et al. |
| 5,938,668 A | 8/1999 | Scirica et al. |
| 5,954,732 A | 9/1999 | Hart et al. |
| 5,984,917 A * | 11/1999 | Fleischman et al. ............ 606/32 |
| 6,068,603 A | 5/2000 | Suzuki |
| 6,071,263 A | 6/2000 | Kirkman |
| 6,106,510 A * | 8/2000 | Lunn et al. .................... 604/525 |
| 6,245,079 B1 | 6/2001 | Nobles et al. |
| 6,319,263 B1 | 11/2001 | Levinson |
| 6,402,740 B1 | 6/2002 | Ellis et al. |
| 6,491,707 B2 | 12/2002 | Makower et al. |
| 6,517,498 B1 | 2/2003 | Burbank et al. |
| 6,520,214 B1 | 2/2003 | Sugiyama et al. |
| 6,551,329 B1 | 4/2003 | Kortenbach et al. |
| 6,638,234 B2 | 10/2003 | Burbank et al. |
| 6,641,528 B2 | 11/2003 | Torii |
| 6,689,130 B2 | 2/2004 | Arai et al. |
| 6,758,848 B2 | 7/2004 | Burbank et al. |
| 6,837,846 B2 * | 1/2005 | Jaffe et al. .................... 600/114 |
| 6,939,349 B2 | 9/2005 | Fleischman et al. |
| 7,033,315 B2 | 4/2006 | Smith |
| 7,118,569 B2 | 10/2006 | Snay et al. |
| 7,201,731 B1 | 4/2007 | Lundquist et al. |
| 7,250,027 B2 | 7/2007 | Barry |
| 7,455,675 B2 | 11/2008 | Schur et al. |
| 7,575,568 B2 * | 8/2009 | Holman et al. ............ 604/96.01 |
| 7,578,786 B2 | 8/2009 | Boulais et al. |
| 7,828,790 B2 | 11/2010 | Griffin |
| 7,846,179 B2 | 12/2010 | Belef et al. |
| 2001/0049497 A1 | 12/2001 | Kalloo et al. |
| 2002/0022851 A1 | 2/2002 | Kalloo et al. |
| 2002/0111534 A1 | 8/2002 | Suzuki et al. |
| 2002/0165589 A1 | 11/2002 | Imran et al. |
| 2003/0009085 A1 * | 1/2003 | Arai et al. .................... 600/127 |
| 2003/0083550 A1 | 5/2003 | Miyagi |
| 2003/0130560 A1 | 7/2003 | Suzuki et al. |
| 2003/0229296 A1 | 12/2003 | Ishikawa et al. |
| 2003/0236535 A1 | 12/2003 | Onuki et al. |
| 2004/0050395 A1 | 3/2004 | Ueda et al. |
| 2004/0059350 A1 | 3/2004 | Gordon et al. |
| 2004/0127917 A1 | 7/2004 | Ginn |
| 2004/0193016 A1 * | 9/2004 | Root et al. .................... 600/146 |
| 2004/0231683 A1 | 11/2004 | Eng et al. |
| 2004/0249392 A1 | 12/2004 | Mikkaichi et al. |
| 2005/0107663 A1 * | 5/2005 | Saadat et al. .................... 600/104 |
| 2005/0125021 A1 * | 6/2005 | Nance et al. .................... 606/192 |
| 2005/0137453 A1 | 6/2005 | Ouchi et al. |
| 2005/0165272 A1 | 7/2005 | Okada et al. |
| 2005/0236277 A9 * | 10/2005 | Imran et al. .................... 205/317 |
| 2005/0250986 A1 | 11/2005 | Rothe et al. |
| 2005/0288688 A1 | 12/2005 | Sakamoto et al. |

OTHER PUBLICATIONS

U.S. Office Action dated Jun. 8, 2010 received in related U.S. Appl. No. 11/435,182.
U.S. Office Action dated Oct. 26, 2009 received in related U.S. Appl. No. 11/649,099.
U.S. Office Action dated Dec. 3, 2009 received in related U.S. Appl. No. 11/358,257.
U.S. Office Action dated Aug. 25, 2010, in related U.S. Appl. No. 11/649,036.
European Search Report for European Patent Application No. 10010338.1-1526, mailed Nov. 2, 2010.
Office Action mailed Jan. 10, 2011 in related U.S. Appl. No. 12/103,441.
U.S. Office Action mailed Jan. 31, 2011, in related U.S. Appl. No. 11/649,099.
U.S. Office Action mailed on Mar. 30, 2010 in related U.S. Appl. No. 11/331,938.
U.S. Office Action, mailed on Sep. 7, 2011 in U.S. Appl. No. 11/360,198.
U.S. Office Action mailed, on Oct. 11, 2011 in related U.S. Appl. No. 11/649,036.
U.S. Office Action mailed on May 24, 2011 in related U.S. Appl. No. 11/649,036.
U.S. Office Action mailed on May 26, 2011 in related U.S. Appl. No. 12/103,441.
U.S. Office Action mailed on Jul. 12, 2011 in related U.S. Appl. No. 11/435,182.
U.S. Office Action mailed on Jul. 21, 2011 in related U.S. Appl. No. 11/649,099.
U.S. Office Action, mailed on Jul. 3, 2012 in related U.S. Appl. No. 12/958,867.
U.S. Office Action, mailed on Jan. 17, 2013 in related U.S. Appl. No. 11/435,182.
U.S. Office Action dated Dec. 29, 2009, received in related U.S. Appl. No. 11/371,565.
U.S. Office Action, mailed on Mar. 29, 2012 in related U.S. Appl. No. 11/435,182.
U.S. Office Action dated Mar. 27, 2013 in related U.S. Appl. No. 11/649,036.
U.S. Office Action, mailed on Aug. 27, 2012 in related U.S. Appl. No. 11/649,099.
U.S. Office Action dated Dec. 2, 2013 in related U.S. Appl. No. 12/103,441.

* cited by examiner

US 8,721,657 B2

MEDICAL INSTRUMENT

CROSS-REFERENCE TO RELATED APPLICATION

This is a Continuation-in-Part application of U.S. patent application Ser. No. 11/649,099, filed Jan. 3, 2007, and entitled "OVERTUBE AND ENDOSCOPIC TREATMENT SYSTEM", which is a Continuation-in-part application of U.S. patent application Ser. No. 11/331,938, filed Jan. 13, 2006 now abandoned, and entitled "OVERTUBE AND ENDOSCOPIC TREATMENT SYSTEM", the contents of these applications are entirely incorporated herein by reference.

BACKGROUND OF THE INVENTION

1. Field of the Invention

This invention relates to a medical instrument which is inserted into a body cavity and performs a bending operation.

2. Description of Related Art

Laparoscopic operations are known in which, in performing a medical procedure of observing, treating, etc. an organ of the human body, instead of incising the abdominal wall widely, a plurality of orifices are opened in the abdominal wall and procedures are performed upon inserting a laparoscope, forceps, and other treatment instruments into the orifices. Such procedure provides the benefit of lessening the burden placed on the patient because only small orifices need to be opened in the abdominal wall.

In recent years, methods of performing procedures upon inserting a flexible endoscope via the mouth, nose, anus, or other natural orifice of the patient have been proposed as methods of further reducing the burden on the patient. An example of such procedures is disclosed in U.S. Pat. No. 5,458,131.

With this method, a flexible endoscope is inserted from the mouth of a patient, an opening is formed in the stomach wall, and a distal end part of the endoscope is fed into the abdominal cavity from the opening. Then while using the endoscope as a device for observing the interior of the abdominal cavity, desired procedures are performed inside the abdominal cavity using a treatment instrument inserted through the endoscope or a treatment instrument inserted from another opening.

SUMMARY OF THE INVENTION

In accordance with an aspect of the present invention, a medical instrument for performing a medical procedure within a body cavity includes: an insertion part which is inserted into the body cavity and has a bending part capable of bending in a predetermined range; a manipulating part which manipulates the bending part; a wire which connects the bending part with the manipulating part; and a clutch which is provided in the manipulating part and maintains a bending state of the bending part.

DETAILED DESCRIPTION OF THE INVENTION

Figure 1:
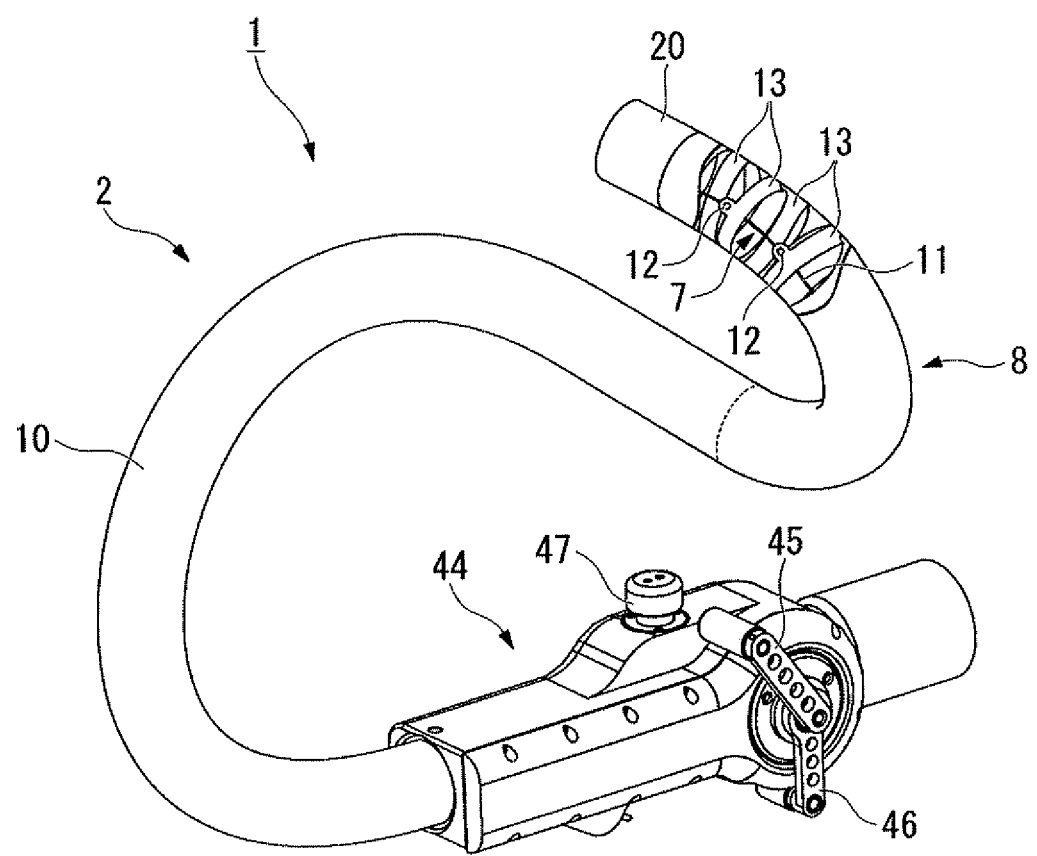
FIG. 1 is a schematic view of an entirety of an overtube according to a first embodiment.

Embodiments according to the present invention will now be described in detail below. In the following description, components that are the same shall be provided with the same numeric symbol and redundant description shall be omitted.

First Embodiment

An endoscopic treatment system 1 according to the present embodiment, as shown in FIG. 1 to FIG. 11, includes: an overtube 2; an endoscope (device) 3 that is inserted in the overtube 2 for carrying out a medical procedure inside a body; and a puncture needle 6 that is inserted through treatment instrument insertion channels 58 and 60 described below that are provided in an endoscope inserting part (device inserting part) 5 of the endoscope 3 whose distal end bends freely, and the distal end of the puncture needle splits apart to be wider than the inner diameter of the treatment instrument insertion channels 58 and 60.

An overtube 2 is used as a guide tube for inserting the endoscope 3 into a body. The overtube 2 includes: an insertion part 10 that is inserted into a stomach or other hollow organ or abdominal cavity, etc., of a patient (subject) and has a lumen 7 through which the endoscope inserting part 5 is removably inserted and a bending part 8 that bends the distal end side of the lumen 7; and a bending wire 11 for performing a bending operation of the bending part 8.

Figure 2:
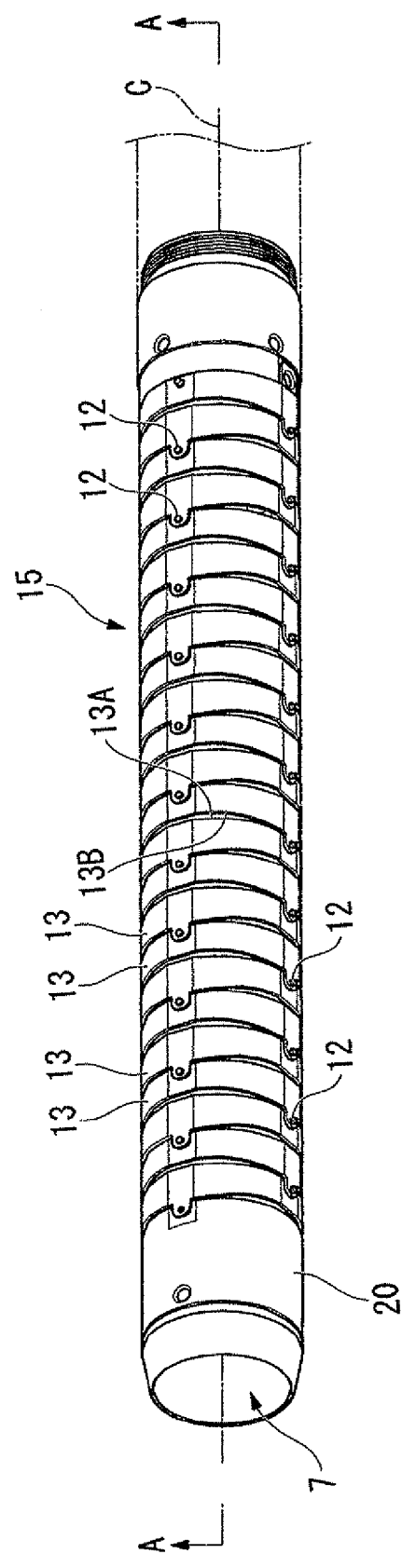
FIG. 2 is a view of the principal portions of the overtube according to the first embodiment.
Figure 3:
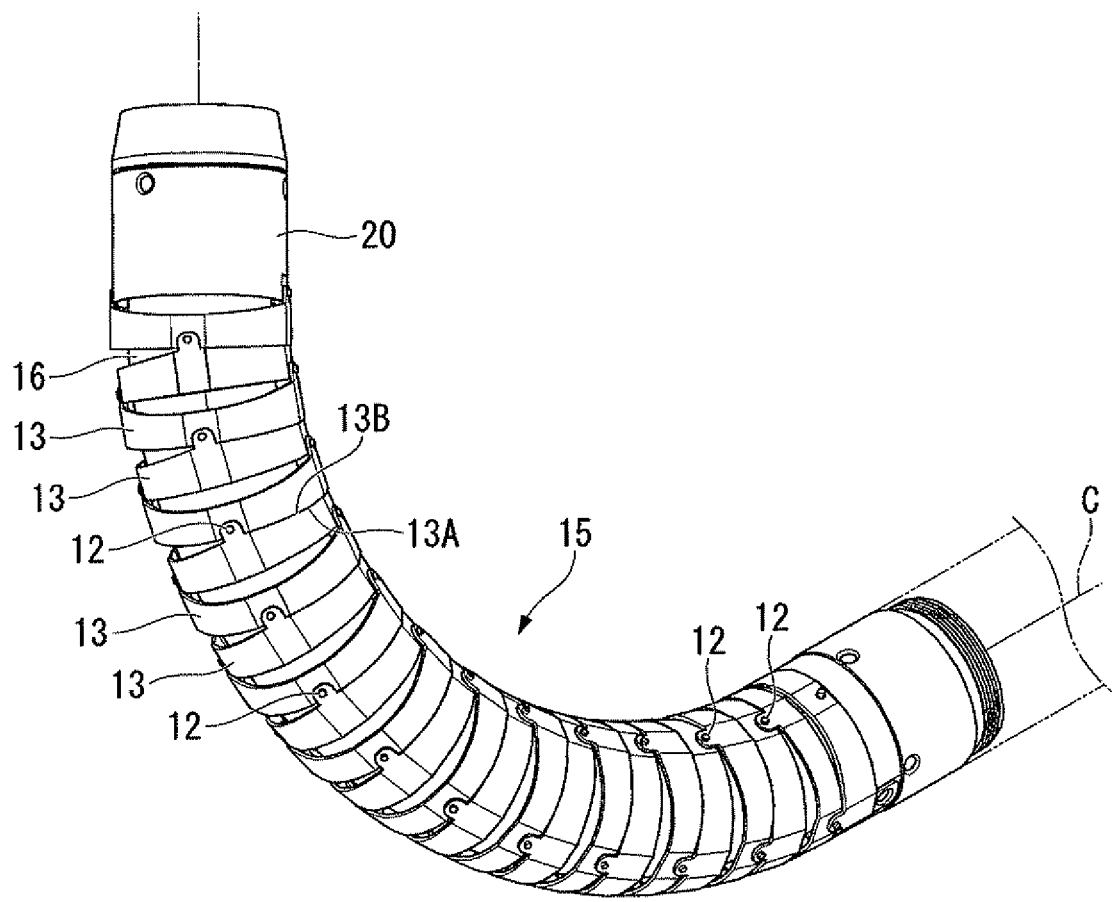
FIG. 3 is a view of the principal portions of the overtube according to the first embodiment.
Figure 4:
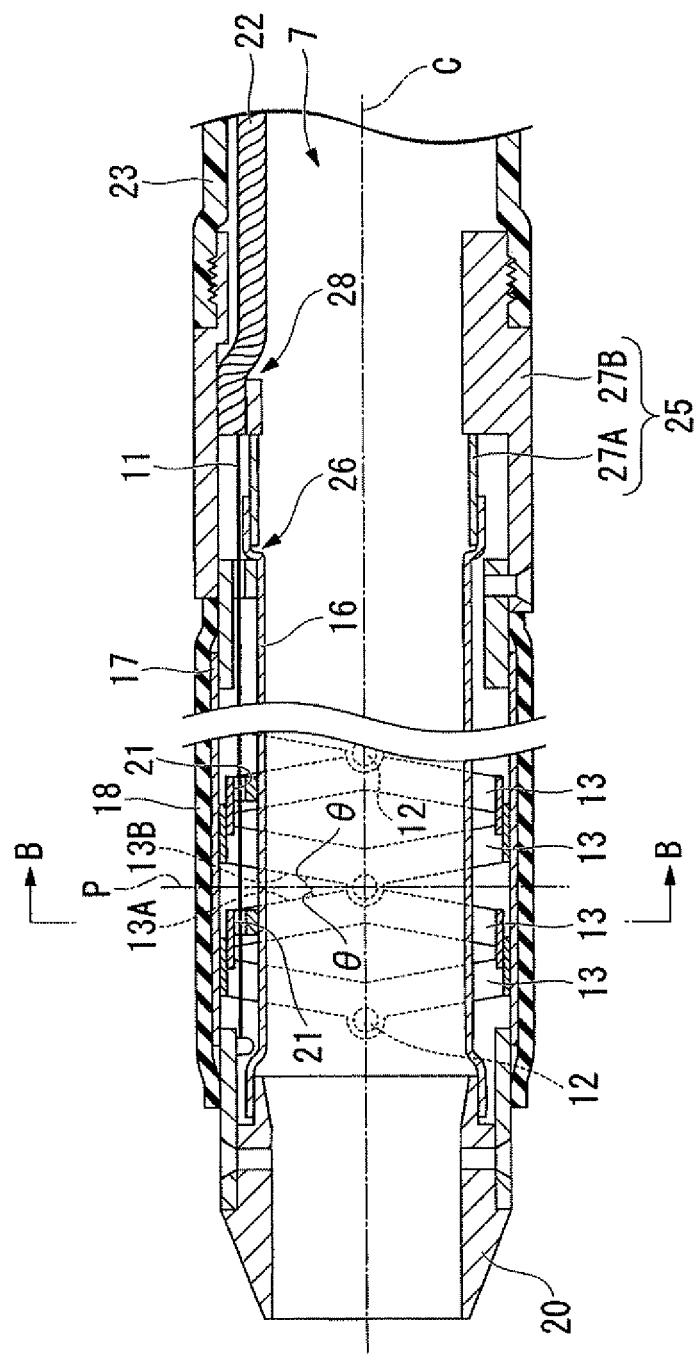
FIG. 4 is a sectional view taken along line A-A of FIG. 2.

The bending part 8 is disposed on the distal end side of the insertion part 10 and, as shown in FIG. 2 to FIG. 4, includes a bending tube 15 that has of a plurality of ring-shaped joint rings 13 that are mutually connected via connecting shafts 12 along the lumen 7 to freely turn; a tubular inner braid (braided tube) 16 that is disposed on the inner side of the bending tube 15 and forms the periphery of the lumen 7; a tubular outer braid 17 that covers the periphery of the bending tube 15; and a resin outer skin 18 that constitutes the outermost layer of the bending part 8. A tubular distal end part 20 to which the distal end of the bending wire 11 is connected is connected to the distal end of the bending part 8.

Each joint ring 13 has a proximal-end side first surface 13A and a distal-end side second surface 13B. When the bending tube 15 bends, with respect to a virtual plane P that includes the connecting shafts 12 and is perpendicular to a central axis line C of the lumen 7, the first surface 13A and the second surface 13B incline respectively at a predetermined angle θ in the direction of the central axis C. When the bending tube 15 bends, the first surface 13A of the joint ring 13 and the second surface 13B of the adjacent joint ring 13 abut. Here, since the angle θ is an angle smaller than that of ordinary joint rings not shown that the endoscope inserting part 5 has, the gap between the joint rings 13 is narrower than usual. Also, in order to ensure the bending range of the bending tube 15, the number of joint rings 13 is more than normal.

Figure 5:
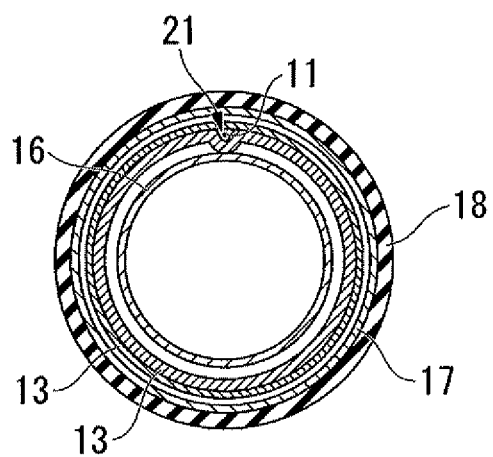
FIG. 5 is a sectional view taken along line B-B of FIG. 4.

On the joint ring 13, a pass-through part 21 is provided for the bending wire 11 to pass through the bending tube 15 along the central axis C. The pass-through part 21, as shown in FIG. 5, is formed with a portion of the joint ring 13 being bent inward in the radial direction. For that reason, a portion of the inner braid 16 is mounted in a deformed state by being pressed inward in the radial direction by the pass-through part 21. The pass-through part 21 is provided at only one location. That is, one bending wire 11 only is disposed in the pass-through part 21. The bending tube 15 is constituted to bend only in the direction in which the side on which the bending wire 11 is inserted serves as the inner side in the radial direction. The bending wire 11 is disposed to freely advance and retract in a coil tube 22 further to the proximal end side than the bending part 8.

The insertion part 10 further to the proximal end side than the bending part 8 is covered by a resin layer 23. The distal end of the resin layer 23 and the bending part 8 are connected via a connecting part 25. The connecting part 25 is provided with an inner tube part 27A, on which the proximal end of the outer braid 17 is externally fitted, and an outer tube part 27B, on which the proximal end of the outer skin 18 is bonded and the distal end of the resin layer 23 is screw fitted. The inner tube part 27A is provided with a first slit 26 that sandwiches the proximal end of the inner braid 16, and the outer tube part 27B is provided with a second slit 28 that sandwiches the distal end of the coil tube 22.

Figure 6:
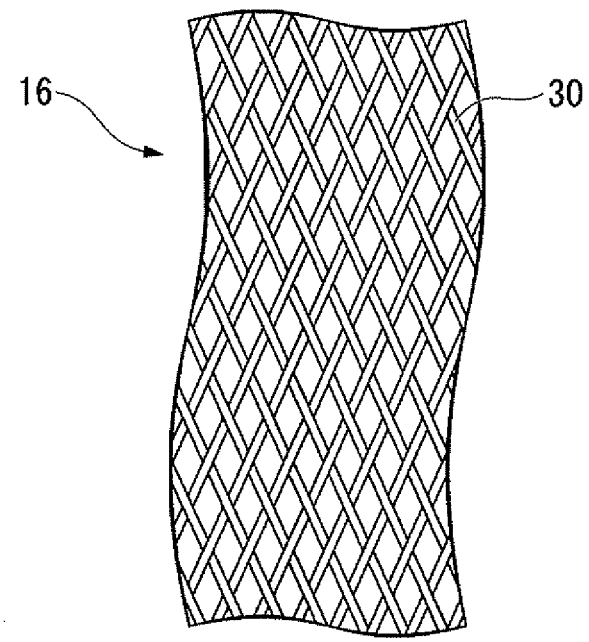
FIG. 6 is a view showing the constitution of the inner braid of the overtube according to the first embodiment.

The inner braid 16 and the outer braid 17, as shown in FIG. 6, are formed by braiding one thin metallic wire 30 so as to intersect with the central axis C. For that reason, the gaps that are formed between the joint rings 13 are blocked by the inner braid 16.

Figure 7:
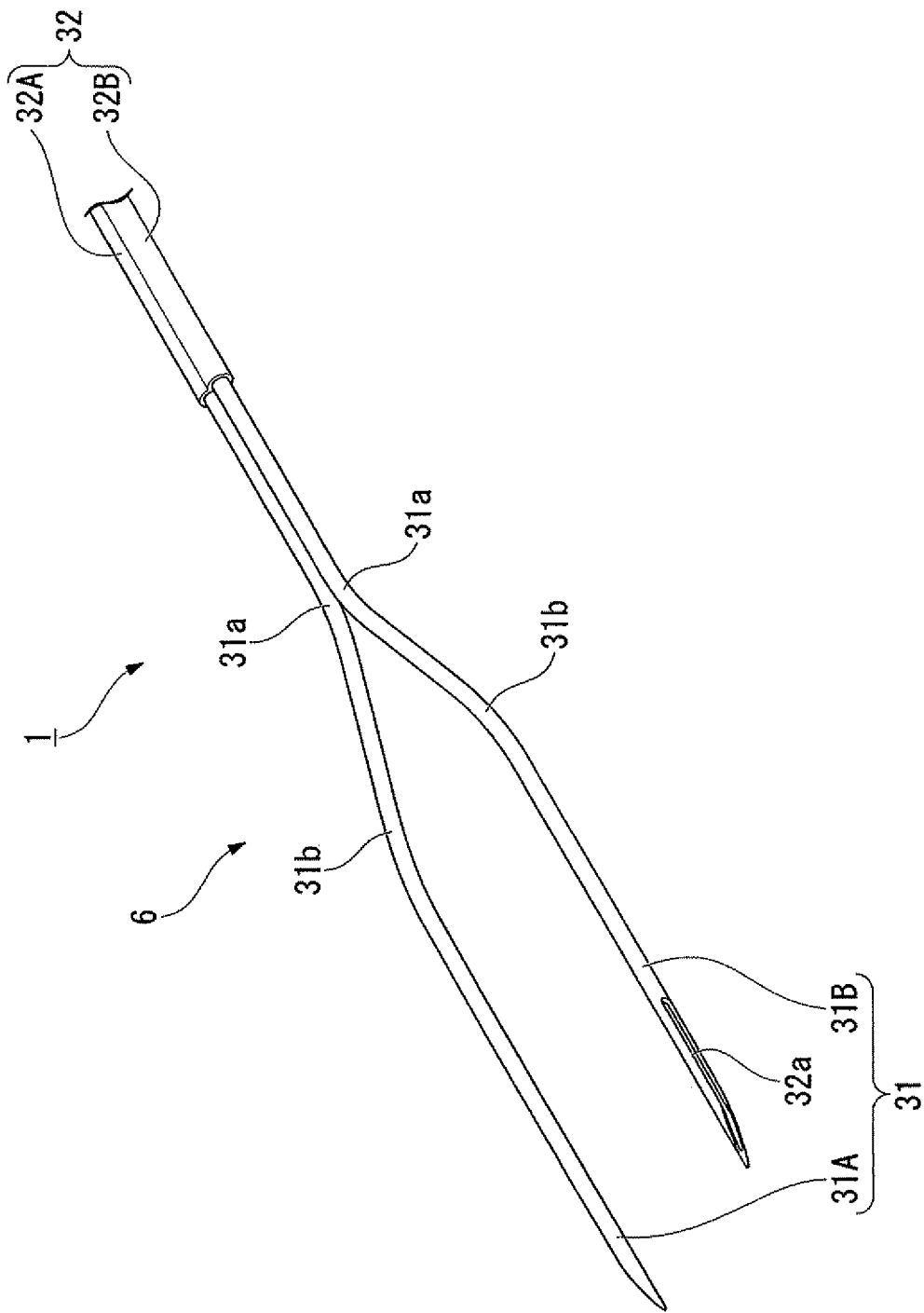
FIG. 7 is a view showing the principal portions of the puncture needle used with the endoscope system according to the first embodiment.

As shown in FIG. 7, the puncture needle 6 includes: a needle part 31 that has a metal first needle part 31A and a second metal needle part 31B that are hollow and spaced apart; and a sheath 32 that has a first sheath 32A and a second sheath 32B that respectively accommodate the first needle part 2A and the second needle part 2B to freely protrude and retreat.

The first needle part 31A and the second needle part 31B are each provided with a bend part 31a that separates a distal end side of the first needle part 31A and the second needle part 31B to be further apart than the gap between a proximal end side thereof. Further to the distal end side than the bend part 31a of the first needle part 31A and the second needle part 31B is also provided an alignment part 31b that disposes the distal end sides of the first needle part 31A and the second needle part 31B to be mutually parallel. A slit 32a through which a suture 33C described below passes is formed at the distal end of the first needle part 31A and the second needle part 31B. The bend part 31a and the alignment part 31b resiliently deform to be accommodated in the sheaths 32A and 32B when accommodating the needle parts 31A and 31B in the sheaths 32A and 32B. At least the distal end sides of the sheaths 32A and 32B are integrated so as not to come apart.

Figure 8:
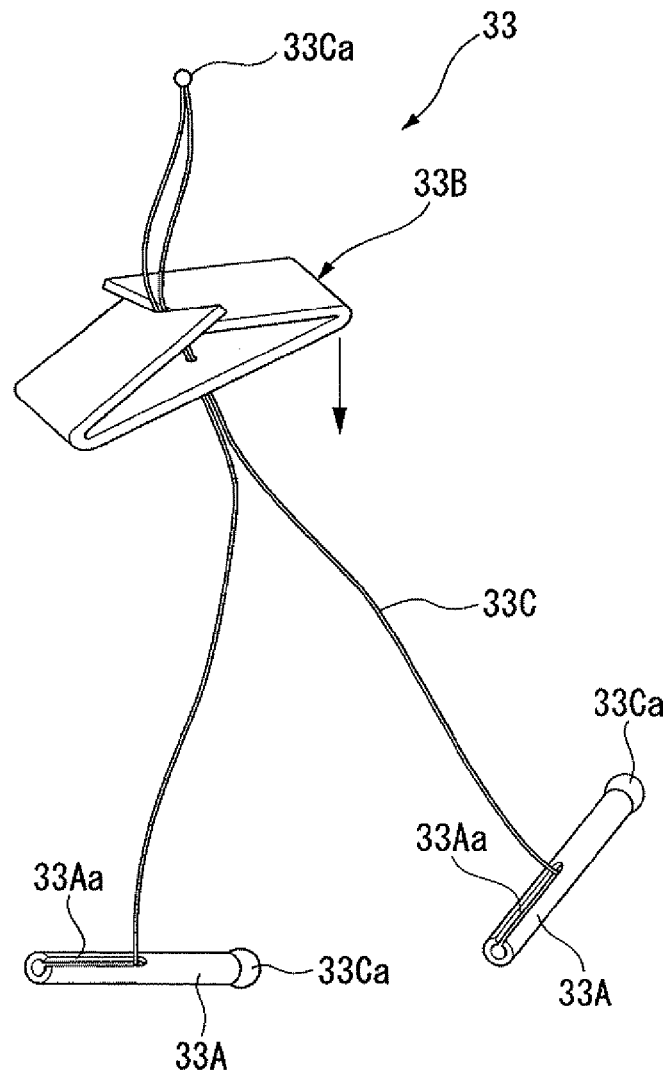
FIG. 8 is an overall view of the double T-bars used with the endoscope system according to the first embodiment.
Figure 9:
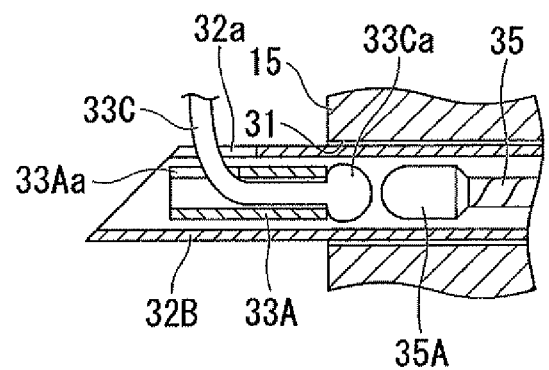
FIG. 9 is a sectional view of a state in which the double T-bars are fitted into a puncture needle according to the first embodiment.

Two anchors 33A of double T-bars 33, shown in FIG. 8, are respectively held inside the respective needle parts 31A and 31B. The double T-bars 33 have two sutures 33C, one end side of each of which is passed through a substantially triangular stopper 33B. At one end, the sutures 33C are bound together to for a large diameter part 33Ca. Each of the other ends of the sutures 33C is fixed to the anchors 33A. Each anchor 33A has a cylindrical shape with a slit formed at an end, and the suture 33C is inserted in the longitudinal direction of the interior of the anchor 33A through the slit. The large diameter part 33Ca that has greater diameter than that of the anchor 33A is formed at the other end of the suture 33C. The stopper 33B has a hole, through which the sutures 33C are passed, at a center in the longitudinal direction of an elongated, thin plate member. The respective ends in the longitudinal direction of the stopper 33B are folded obliquely and sandwich the sutures 33C. The respective ends in the longitudinal direction of the stopper 33B are cut to notches of triangular shape. With the stopper 33B, the respective ends are folded back obliquely so that the notches intersect and thereby sandwich the sutures 33C. The sutures 33C thus do not fall off from between the ends. When the large diameter part 33Ca of the sutures 33C is pulled in a direction away from the stopper 33B, the respective end parts of the stopper 33B spread apart slightly. The stopper 33B thus allows movement of the sutures 33C in this direction. Meanwhile, when a large diameter part 33Ca at the anchor 33A side of a suture 33C is pulled, a tendency for the suture 33C to move in the direction indicated by the arrow in FIG. 8 arises. However, since the respective ends of the stopper 33B close and grasp the sutures 33C in this process, the suture 33C does not move. A pusher 35 is movably disposed in advancing and retracting directions in the interior of the respective needle parts 31A and 32B. A rigid, pushing member 35A is disposed at a distal end of the pusher 35.

Figure 10:
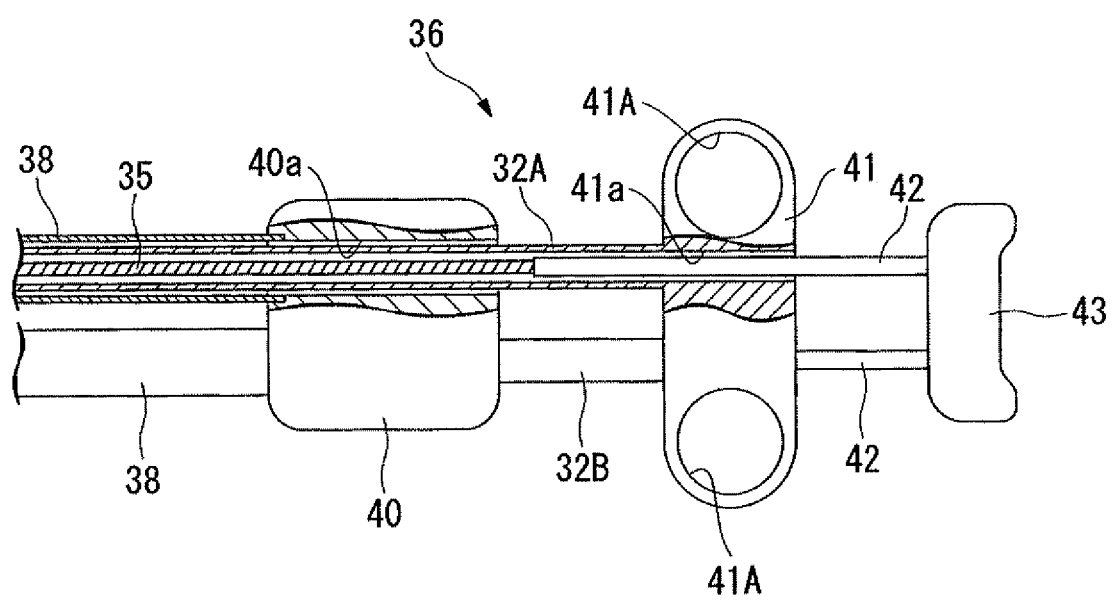
FIG. 10 is a partial sectional view showing the manipulating part of the puncture needle according to the first embodiment.

As shown in FIG. 10, the puncture needle 6 is provided with a needle manipulating part 36 that simultaneously protrudes and retracts the first needle part 31A with respect to the distal end of the first sheath 32A and the second needle part 31B with respect to the distal end of the second sheath 32B. The needle manipulating part 36 includes a sheath holding part 40 connected to the proximal ends of the first sheath 32A and the second sheath 32B; a needle manipulating handle 41 connected to proximal ends of the two needle parts 31A and 31B that have been passed in a manner enabling advancing and retracting through through-holes 40a formed in the sheath holding part 40; and a pusher connection part 43 that connects end portions of rod-like, rigid parts 42, which are passed in a manner enabling advancing and retracting through through-holes 41a formed in the needle manipulating handle 41 and are connected to proximal ends of the two pushers 35, to each other. The needle manipulating handle 41 is provided with finger rings 41A. Each of the needle manipulating handle 41 and the pusher connection part 43 may be divided into two parts so as to enable the two needle parts 31A and 31B and the two pushers 35 to be manipulated independently of each other.

As shown in FIG. 1, a proximal handle 44 having a larger diameter than the insertion part 10 is disposed at the proximal end of the insertion part 10 of the overtube 2. The proximal handle 44 includes a bending lever 45, a bending lock lever 46, and an endoscope lock button 47. The bending lever 45 is connected to the proximal end side of the bending wire 11 for performing bending manipulation of the bending part 8. The bending lock lever 46 is used for fixing the position of the bending lever 45 at an arbitrary position. The endoscope lock button 47 is used for fixing the endoscope 3 with respect to the lumen 7 upon insertion of the endoscope 3 through the lumen 7.

Regarding the endoscope lock button 47, when the endoscope 3 must be fixed to the insertion part 10 upon being inserted through the interior, pressing the endoscope lock button 47 inward in the radial direction presses and fixes the endoscope inserting part 5 in a relative manner by a frictional force. The endoscope lock button 47 may be arranged so as to oppositely release the frictional force when pressed.

Figure 11:
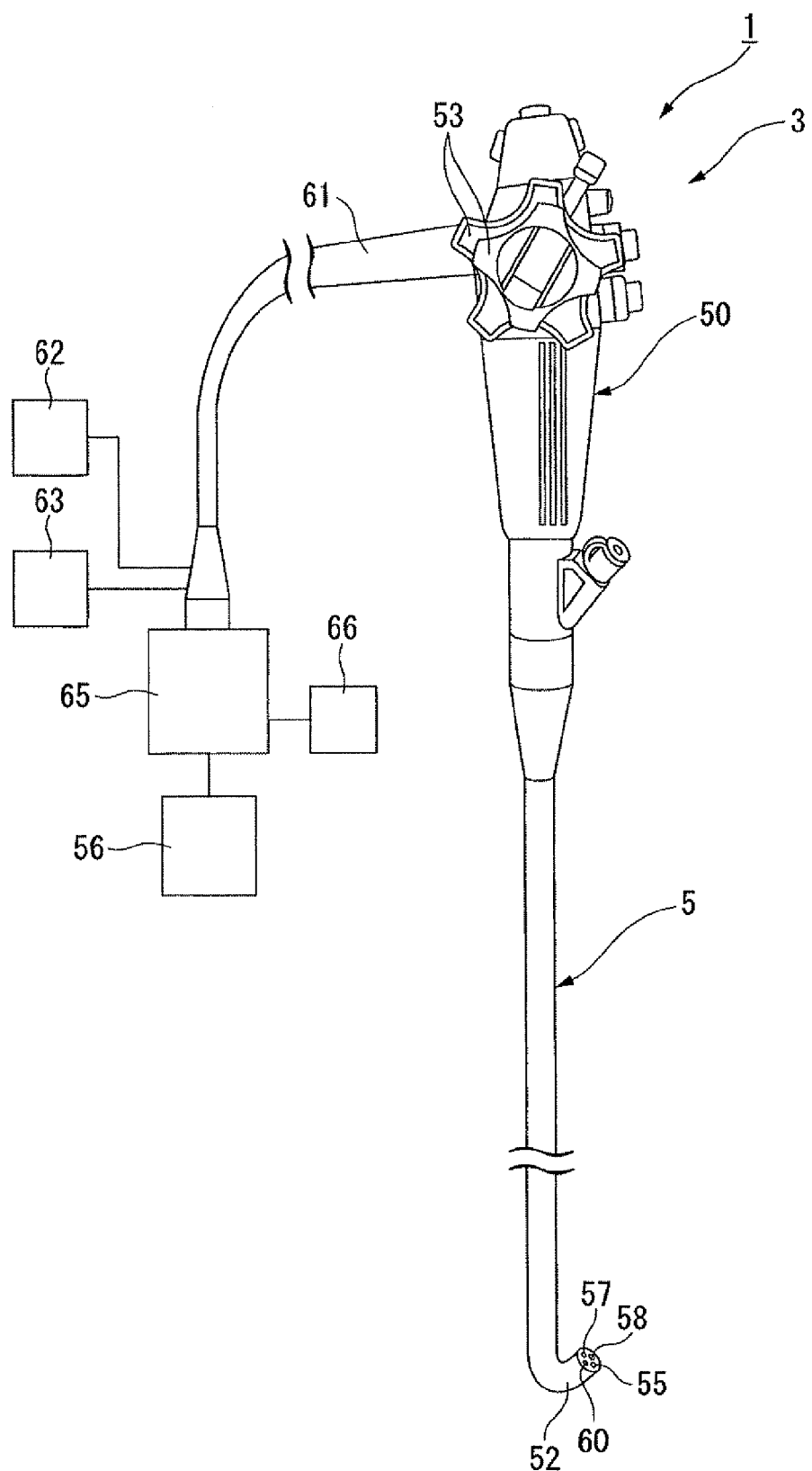
FIG. 11 is an overall schematic view of an endoscope as an example of a device used with the endoscope system according to the first embodiment.

The endoscope 3 to be inserted in the overtube 2 is a flexible endoscope 13 as shown for example in FIG. 11. This endoscope 3 has an endoscope inserting part 5, which is elongated and has flexibility to be inserted into a patient's body, that extends outward from the endoscope manipulating part 50 manipulated by an operator. An endoscope distal end part 52 of the endoscope inserting part 5 can be bent by manipulating an angle knob 53 disposed at the endoscope manipulating part 50. At the endoscope distal end part 52 are disposed an objective lens 55, a distal end face of an optical fiber 57 that guides light from a light source device 56 disposed outside the body, and distal end openings of treatment instrument insertion channels 58 and 60. The treatment instrument insertion channels 58 and 60 are ducts for inserting and removing a treatment instrument. Moreover, the treatment instrument insertion channel 58 is connected via a universal cable 61 to an air/water feeding device 62 or a suction device 63 disposed outside the body. The treatment instrument insertion channel 60 is disposed at a position of six o'clock to eight o'clock of the endoscope inserting part 5.

An observation image input into the objective lens 55 is displayed on a monitor 66 via a control unit 65.

Figure 12:
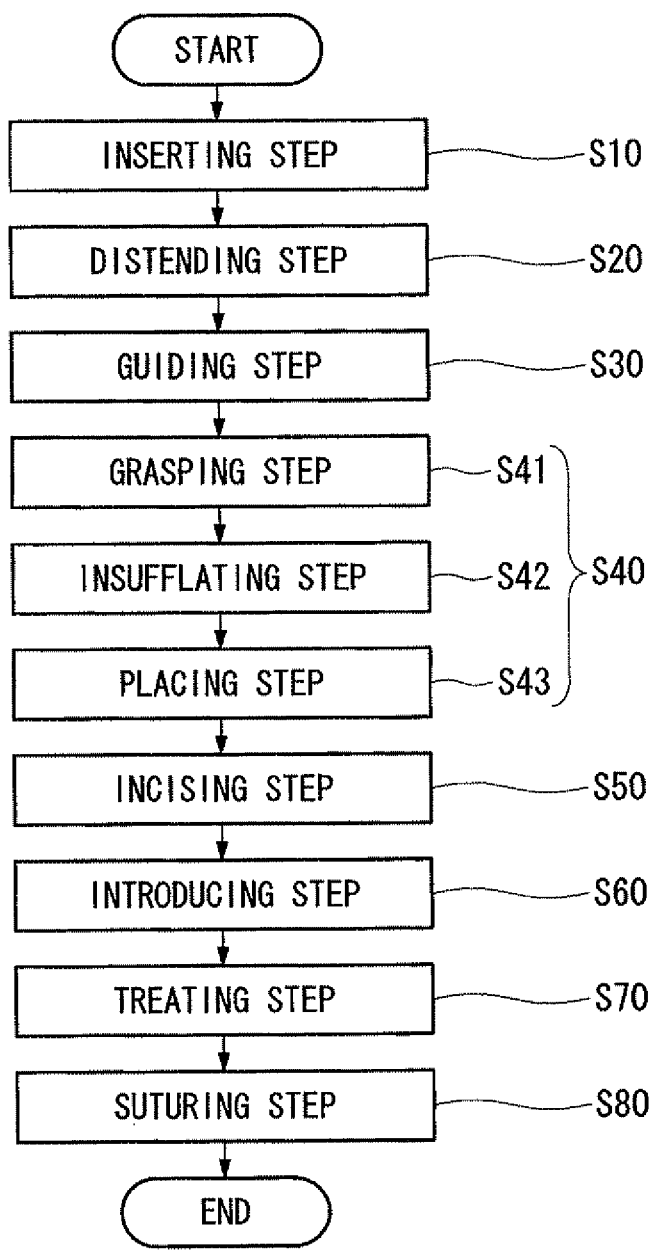
FIG. 12 is a flowchart of a medical procedure according to the first embodiment.

Actions of the present embodiment shall now be described in line with a medical procedure performed via a natural orifice as shown by the flow chart of FIG. 12. In the following description, it shall be deemed that an incision target site is located on an anterior wall of a stomach, and a surgical procedure of inserting the endoscope 3 into the stomach from a mouth of a patient and performing treatment upon forming an opening in the stomach wall and inserting the endoscope inserting part 5 into an abdominal cavity shall be described. Also, though in the embodiment described below, the endoscope 3 is introduced into the body from the mouth of the patient and made to approach the abdominal cavity upon forming the opening in the anterior wall of the stomach, the natural orifice from which the endoscope 3 is introduced is not restricted to the mouth and may be another natural orifice, such as the anus, nose, etc. Furthermore, though the forming of the opening in the anterior wall of the stomach is desirable, this invention is not restricted thereto, and an opening may be formed on the wall of other hollow organ (hollow organ) into which a device is introduced via a natural orifice, such as another area of the stomach, the esophagus, small intestine, or large intestine.

Figure 13:
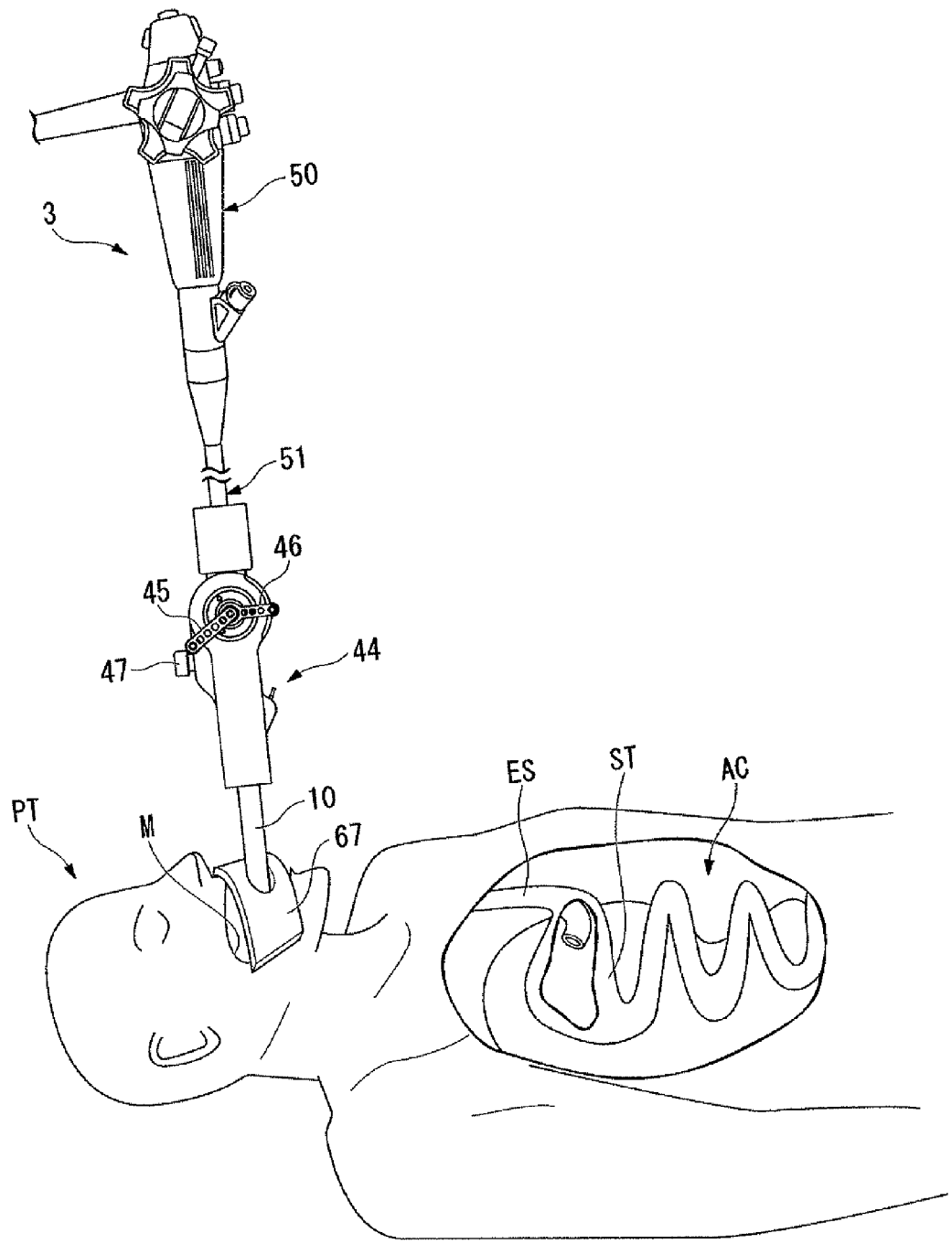
FIG. 13 is a view for describing a state of inserting the endoscope into the overtube in the medical procedure according to the first embodiment.

First, as shown in FIG. 13, with the patient PT being made to lie in a supine position, an inserting step (S10) of inserting the endoscope inserting part 5 through the lumen 7 in the insertion part 10 of the overtube 2 and inserting the insertion part 10 of the overtube 2 and the endoscope inserting part 5 into the stomach ST from the mouth M of the patient PT while observing the interior of the body cavity by means of an endoscopic image is performed. A mouthpiece 67 is fitted onto the mouth of the patient PT and the overtube 2 and the endoscope 3 are inserted, with the endoscope inserting part 5 being inserted through the interior of the lumen 7, into the esophagus ES from the mouthpiece 67.

Here, the inner braid 16 forms the inner periphery of the lumen 7. For this reason, when inserting the endoscope inserting part 5 into the lumen 7, even when the distal end thereof passes the bending part 8, the distal end of the endoscope inserting part 5 does not enter the gaps between the joint rings 13. At this time, since only one pass-through part 21 is provided in the joint rings 13, there is only one location of encroaching the inner diameter of the inner braid 16. Accordingly, a sufficiently large diameter of the lumen 7 is ensured, and so the endoscope inserting part 5 smoothly moves in the lumen 7 with the inner braid 16 serving as a guide.

When bending the bending part 8, the bending wire 11 is pulled toward the proximal side. At this time, the joint rings 13 turn from the distal end side at a predetermined angle about the connecting shafts 12. Thereby, as shown in FIG. 3, bending occurs until the first surface 13A of the joint ring 13 makes contact with the second surface 13B of the opposing joint ring 13. When all the joint rings 13 similarly turn about the connecting shafts 12, the bending part 8 is formed having a prescribed curve.

On the other hand, to extend the bending part 8 so as to make it straight, the bending wire 11 is loosened. At this time, due to the resiliency of the endoscope inserting part 5, torque is added in the direction in which the first surface 13A and the second surface 13B of the joint rings 13 separate. The joint rings 13 thereby turn about the connecting shafts 12 in the opposite direction to the direction during bending, so that, as shown in FIG. 2, the bent bending tube 15 is straightened. Accordingly, the bending part 8 itself also becomes straightened.

Next, in a distending step (S20), air is supplied from the air/water feeding device 62 via the treatment instrument insertion channel 58 of the endoscope inserting part 5 to inflate the stomach ST.

A guiding step (S30) of guiding the insertion part 10 of the overtube 2 to the incision target site T while checking the incision target site T using the endoscope 3, which is also an observation device, is then performed. First, after inserting the endoscope inserting part 5 of the endoscope 3 into the stomach ST, the angle knob 53 is manipulated to bring the distal end of the endoscope inserting part 5 close to the incision target site T while observing the interior of the stomach ST via the objective lens 55, disposed at the endoscope inserting part 5. Then with the incision target site T being specified, the endoscope inserting part 5 is used as a guide to push the insertion part 10 of the overtube 2 and bring the distal end part 20 of the overtube 2 close to the incision target site T.

A needle moving step (S40) of making the needle part 31 of the puncture needle 6 puncture the stomach wall SW and placing the double T-bars 33 is then performed.

Figure 14:
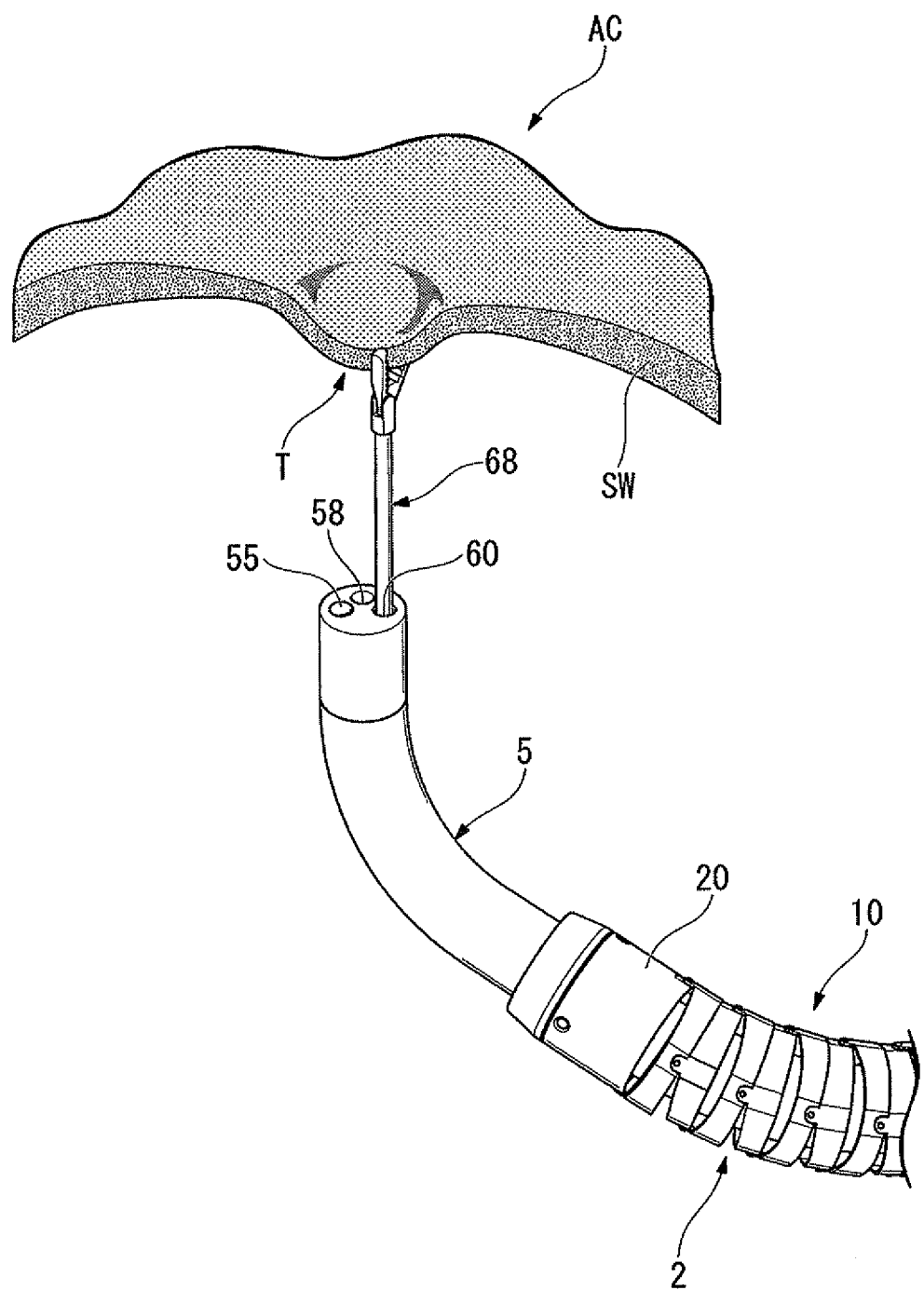
FIG. 14 is a view for describing a state of grasping an incision target site with grasping forceps in the medical procedure according to the first embodiment.

First, in a grasping step (S41), as shown in FIG. 14, the endoscope inserting part 5 is protruded from the distal end part 20 of the overtube 2, and grasping forceps 68 inserted in the treatment instrument insertion channel 60 are further protruded near the incision target site T to grasp the stomach wall SW including the incision target site T. Then, by pulling the grasping forceps 68 into the treatment instrument insertion channel 60, a sufficient space is thereby secured for the abdominal cavity AC on the outer side of the stomach wall SW by making the stomach wall SW concave.

Figure 15:
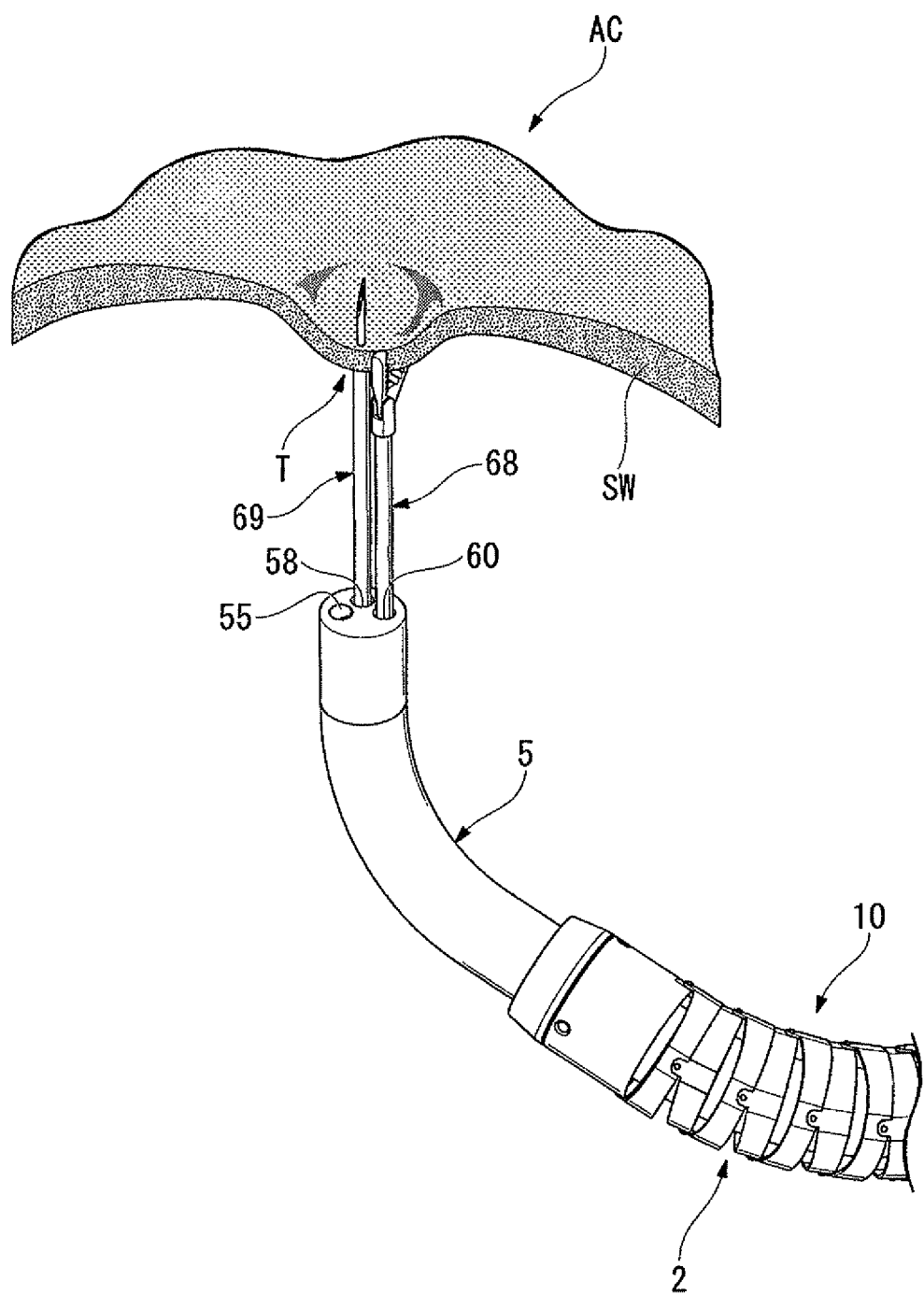
FIG. 15 is a view for describing a state of insufflating by feeding air from an injection needle in the medical procedure according to the first embodiment.
Figure 16:
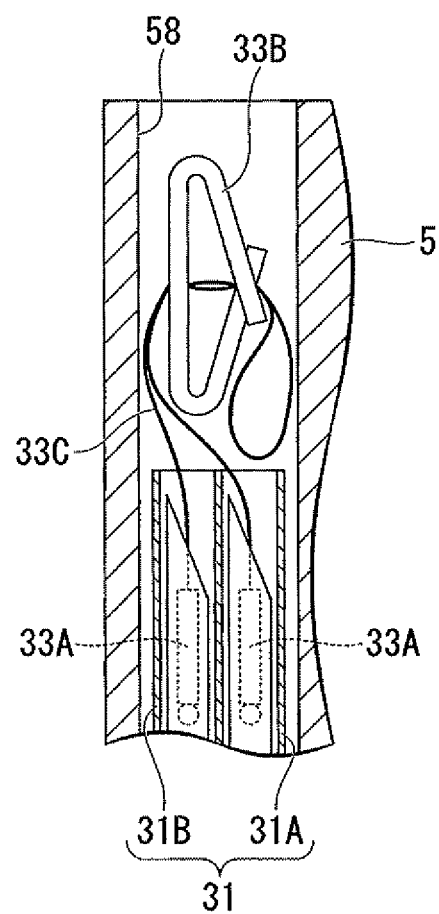
FIG. 16 is a view for describing a state of the puncture needle accommodated in the treatment instrument insertion channel in the medical procedure according to the first embodiment.

An abdominal cavity insulating step (S42) is then performed. First, an injection needle 69 connected to the air/water feeding device not shown is inserted through the treatment instrument insertion channel 58 of the endoscope 3. A distal end of the injection needle 69 is then protruded from the distal end and, as shown in FIG. 15, pierced through the stomach wall SW pulled by the grasping forceps 68 and inserted to the abdominal cavity AC. Because the injection needle 69 is pierced with the stomach SW wall being pulled in and a space being secured with the abdominal wall not shown, just the stomach wall SW can be punctured reliably. Air is then fed into the abdominal cavity AC via the injection needle 69 so that the stomach ST and the abdominal wall not shown separate.

The injection needle 69 preferably has a needle length of approximately 12 mm and more preferably has a bendable distal end to enable piercing of the center of the pulled stomach wall. In this case, a bended injection needle has a bending tendency at a distal end and has a bending wire (not shown) that passes from the distal end toward a proximal side in an inward radial direction of the bending tendency. Here, since the treatment instrument insertion channel 58 of the endoscope 3 is disposed at a position of six o'clock to eight o'clock of the endoscope inserting part 5, the incision site is approached from an upward angle in incising the anterior stomach wall SW of the stomach ST that is preferable as the incision site. Accordingly, since the bending tendency faces the center of the bending wire 11 following the bended state of the insertion part 10 of the overtube 2, the center of the stomach wall can be punctured reliably by pulling the bending wire 11 toward the proximal side. In the process of feeding air, the interior of the abdominal cavity AC may be maintained at an appropriate pressure by monitoring and automatic control of the feed air pressure.

Figure 17:
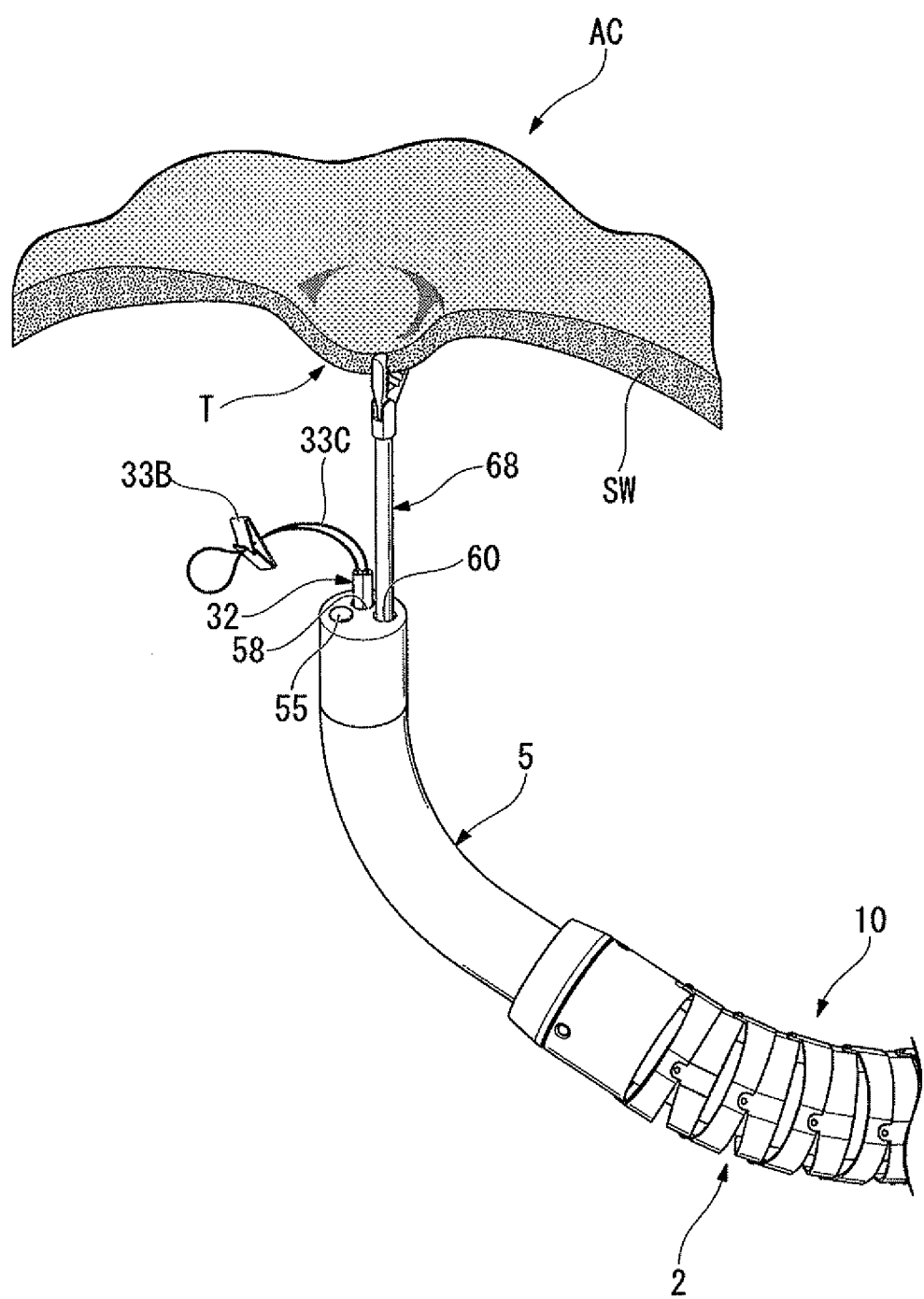
FIG. 17 is a view for describing a state of protruding the puncture needle from the treatment instrument insertion channel in the medical procedure according to the first embodiment.
Figure 18:
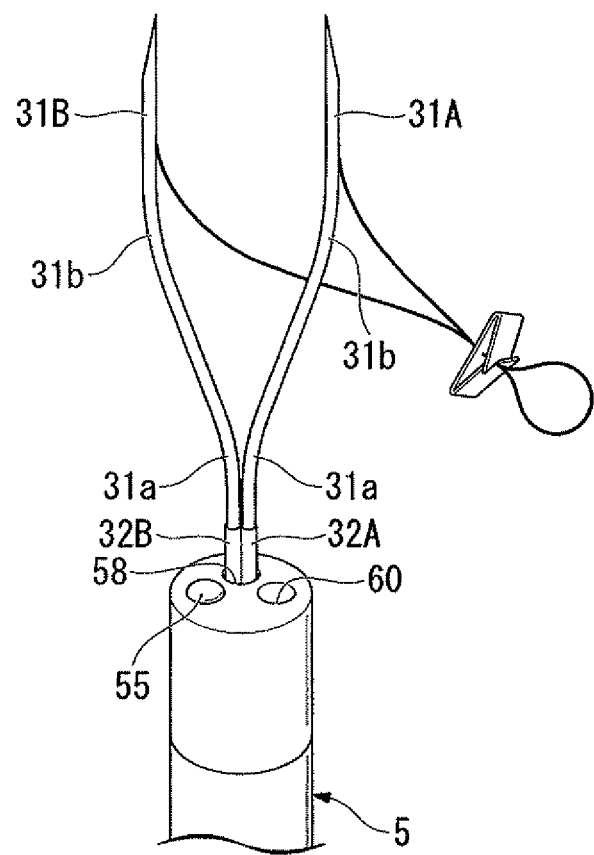
FIG. 18 is a view for describing a state of the double T-bars being retained in the puncture needle in the medical procedure according to the first embodiment.

A placing step (S43) is then performed. Here, first the puncture needle 6 is inserted in the treatment instrument insertion channel 58 instead of the injection needle 69. Then, as shown in FIG. 17, in the vicinity of the incision target site T, the distal end of the sheath 32 is protruded from the treatment instrument insertion channel 58 to be disposed near the stomach wall SW. Moreover, the needle manipulating handle 41 is advanced in the direction of the sheath holding part 40 and, as shown in FIG. 18, the first needle part 31A and the second needle part 31B are protruded from the distal end of the sheath 32, extended separated by a predetermined distance, and proceed to pierce the stomach wall SW. At this time, since a space with the stomach wall SW is secured by insufflation of the abdominal cavity AC, it is possible to puncture only the stomach wall SW.

Figure 19:
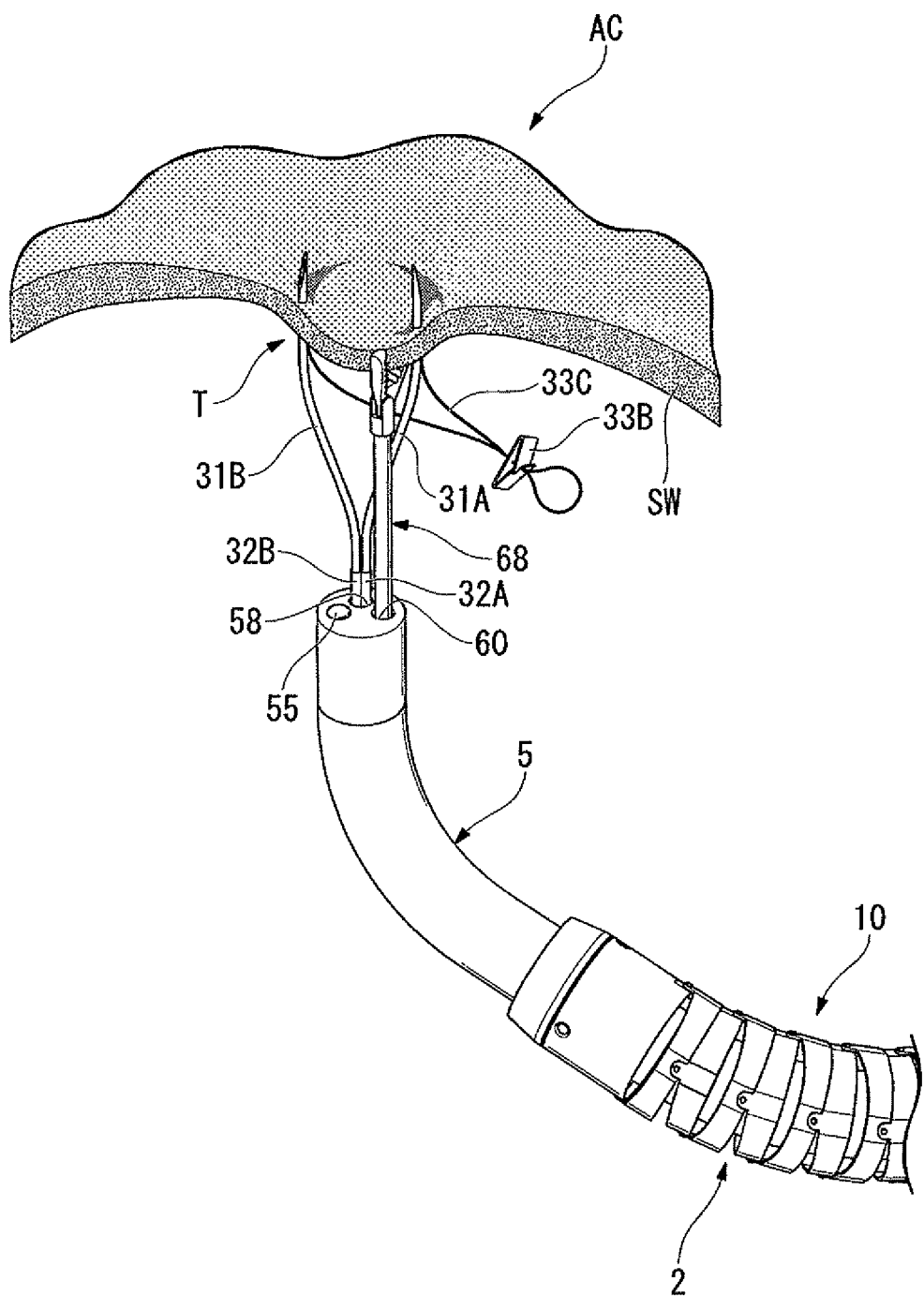
FIG. 19 is a view for describing a state of the puncture needle piercing the incision target site while retaining the double T-bars in the medical procedure according to the first embodiment.

By thus advancing the needle manipulating handle 41, as shown in FIG. 19, two different locations of the stomach wall SW are simultaneously pierced.

The pusher connection part 43 is advanced from this state with respect to the needle manipulating handle 41, and the pusher 35 moves in the distal end direction of the first needle part 31A and the second needle part 31B. At this time, the anchors 33A of the double T-bars 33 are pushed by the pushers 35 to be sent out from within the first needle part 31A and the second needle part 31B to the abdominal cavity AC.

After the anchors 33A of the double T-bars 33 are released, the pusher connection part 43 retracts with respect to the needle manipulating handle 41, and moreover, the needle manipulating handle 41 retracts with respect to the sheath holding part 40, and the first needle part 31A and the second needle part 31B reenter the sheath 32. At this time, the two anchors 33A of the double T-bars 33 open in a T shape due to the bending disposition of the sutures 33C. Thereafter, the entire puncture needle 6 is pulled back to the proximal side, to be withdrawn from the treatment instrument insertion channel 58.

Figure 20:
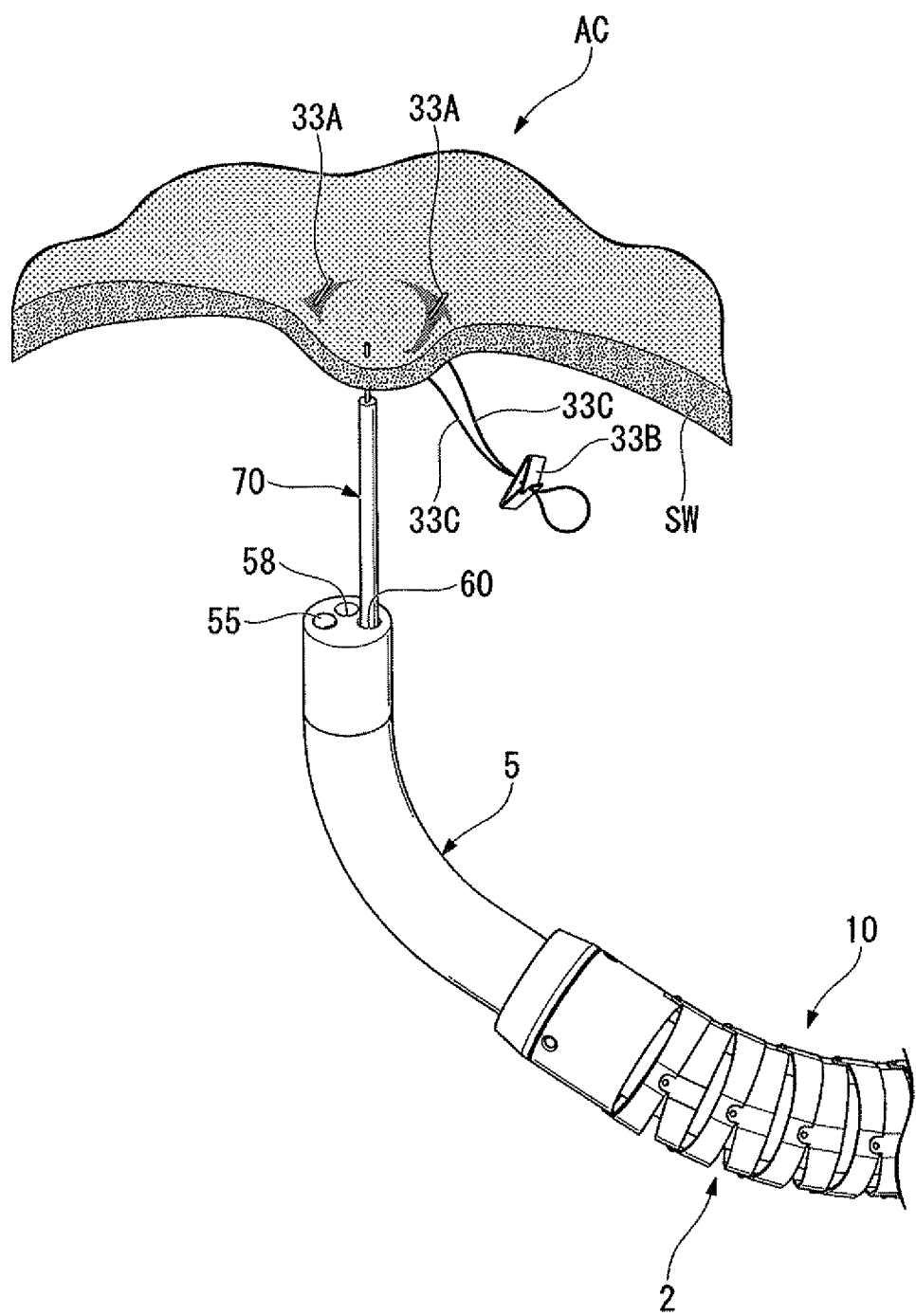
FIG. 20 is a view for describing a state releasing the anchors of the double T-bars from the puncture needle and incising the incision target site with a high-frequency knife in the medical procedure according to the first embodiment.
Figure 21:
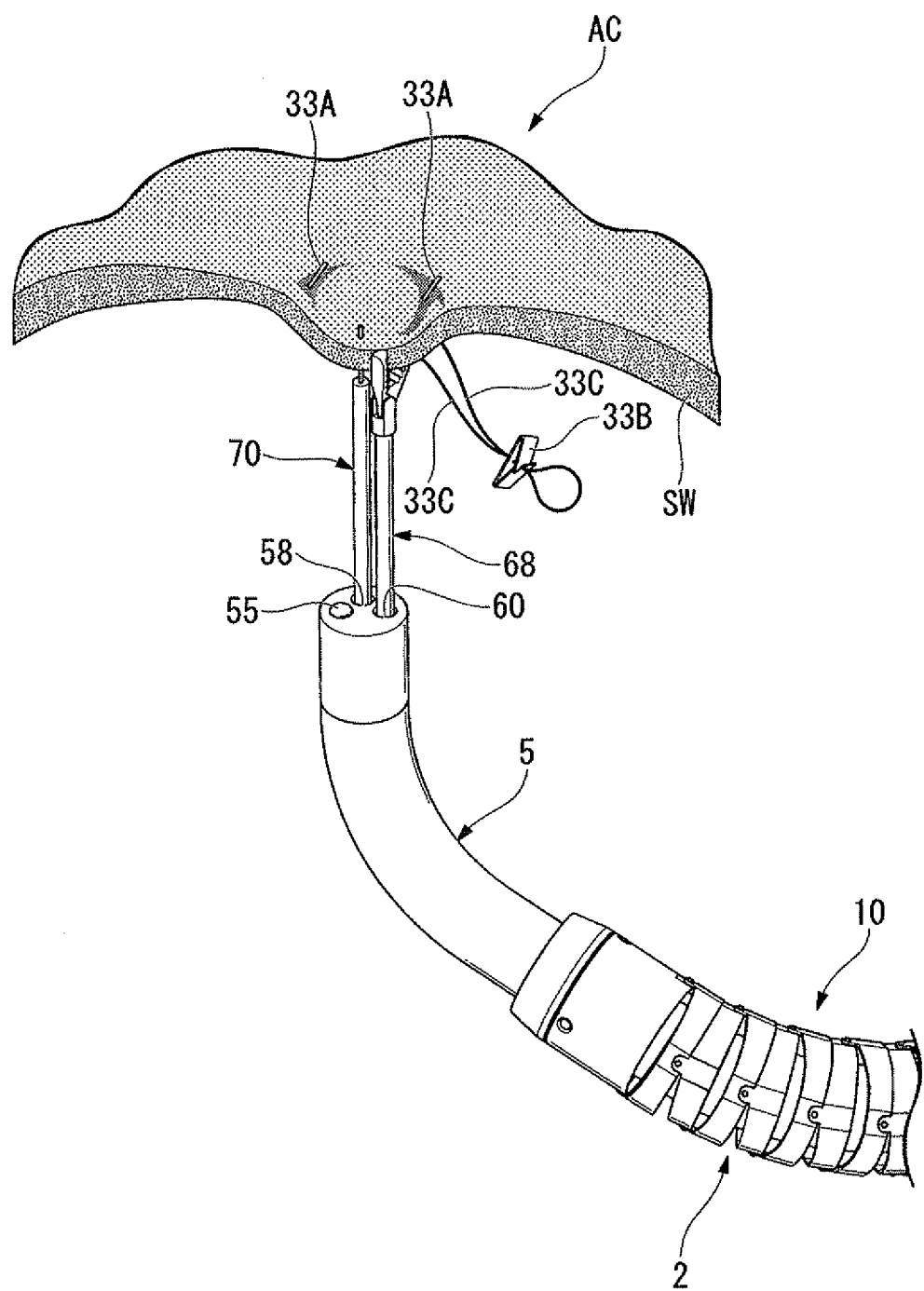
FIG. 21 is a view for describing the state of incising the incision target site while grasping it with the grasping forceps.

The process then proceeds to an incising step (S50). First, a high-frequency knife 70 is inserted through the treatment instrument insertion channel 60 instead of the grasping forceps 68. At this time, it is confirmed that the connection terminal of the power cord is connected to the connection terminal of the electrode manipulating part not shown. Then, high-frequency power is supplied from a high-frequency power source not illustrated in the state of the distal end of the high-frequency knife 70 abutting the stomach wall SW as shown in FIG. 20. As shown in FIG. 21, the high-frequency knife 70 is inserted through the treatment instrument insertion channel 58 in the state of the grasping forceps 68 inserted through the treatment instrument insertion channel 60. While pulling on the stomach wall SW with the grasping forceps 68, the distal end of the high-frequency knife 70 may be made to abut the stomach wall SW with the placement position of the double T-bars 33 and the incision position in an optimal state.

Figure 22:
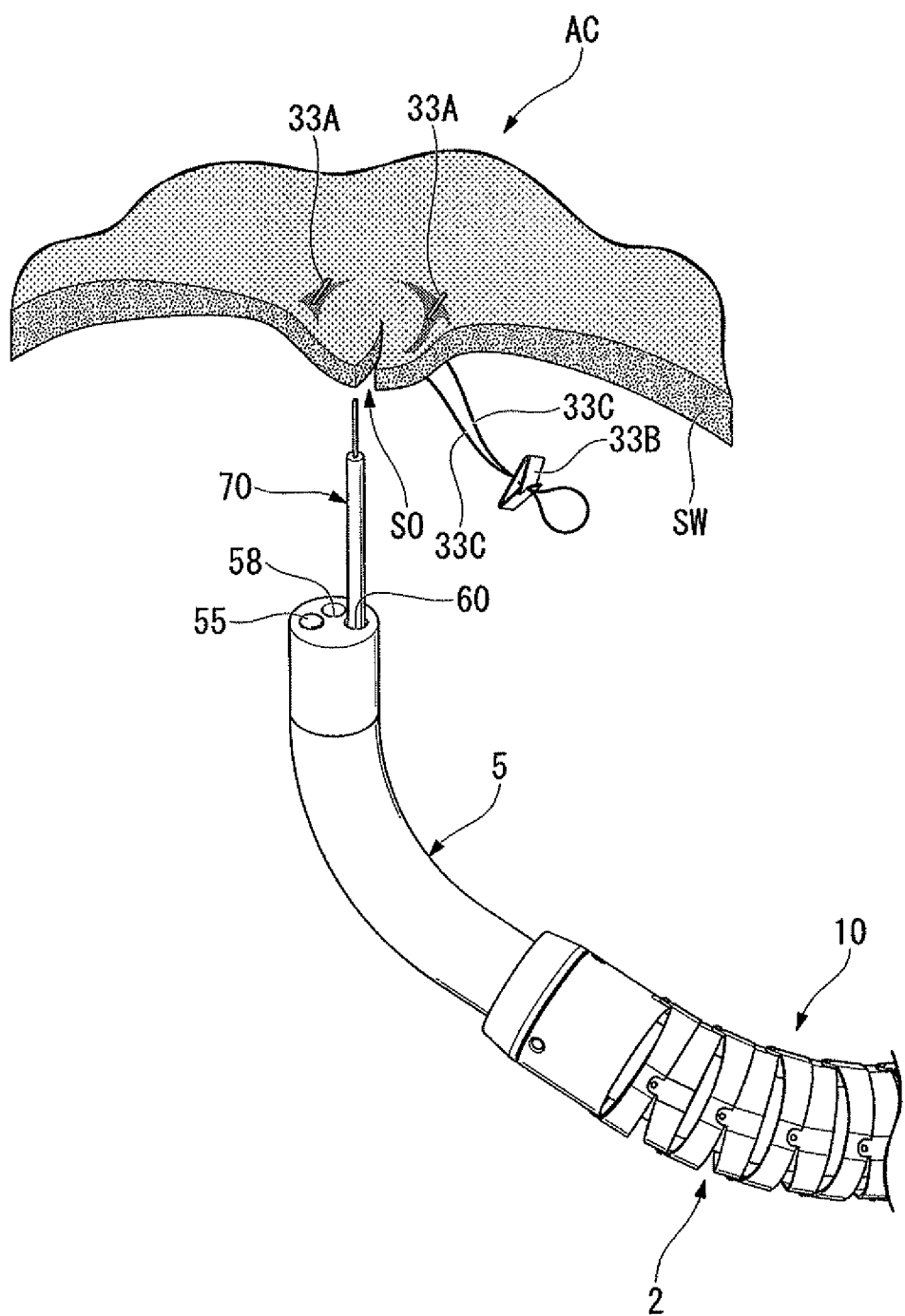
FIG. 22 is a view for describing the state of having incised the incision target site in the case of FIG. 20.
Figure 23:
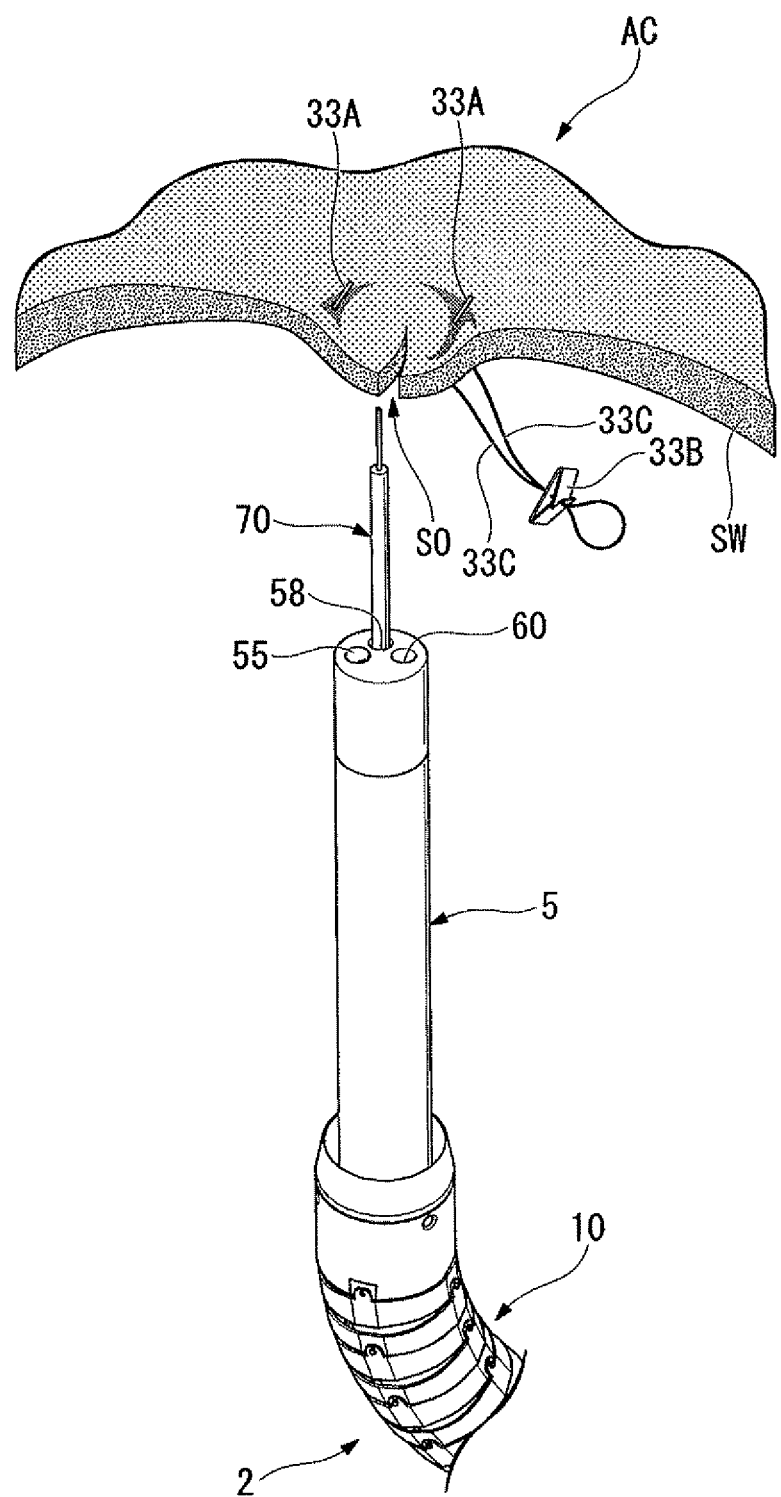
FIG. 23 is a view for describing the state of having incised the incision target site in the case of FIG. 21.

At this time, as shown in FIG. 22 and FIG. 23, the stomach wall SW is incised by the high-frequency knife 70, and an opening SO is formed in the stomach wall SW.

Figure 24:
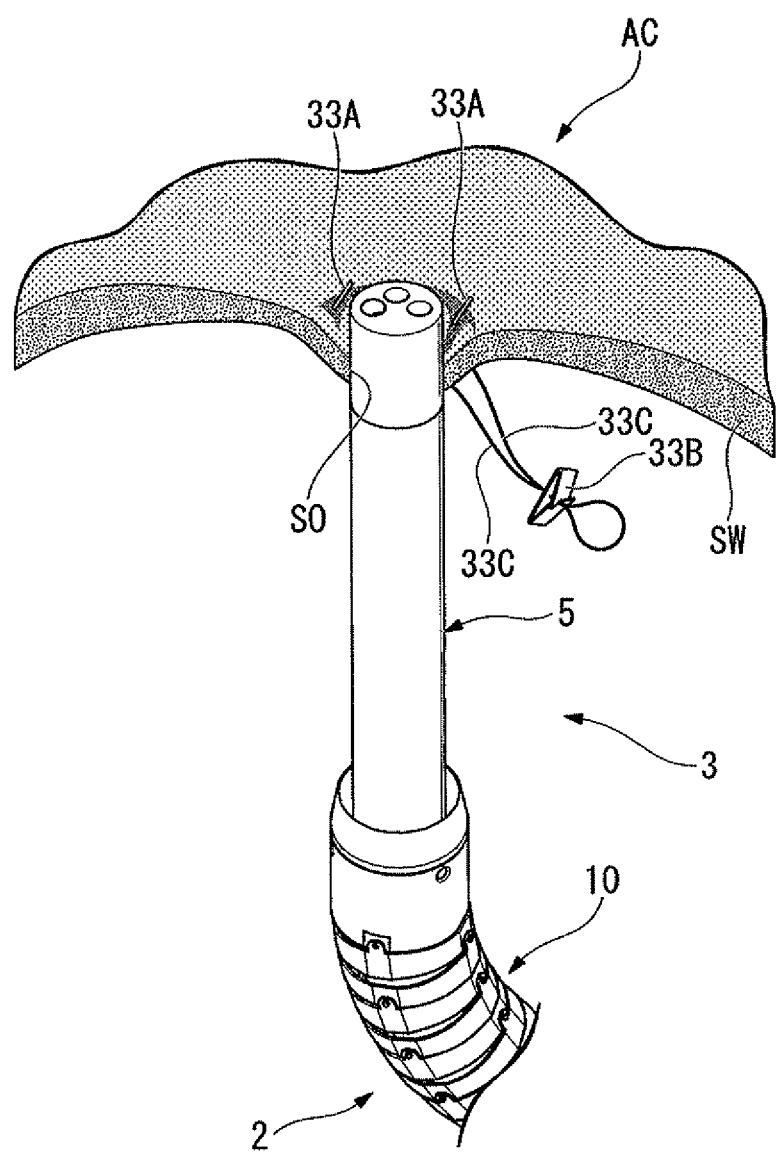
FIG. 24 is a view for describing the state of the endoscope being inserted in the abdominal cavity in the medical procedure according to the first embodiment.

Next, the process proceeds to an introducing step (S60). That is, as shown in FIG. 24, after removing the high-frequency knife 70, the endoscope inserting part 5 of the endoscope 3, which is also an operative device, is introduced into the abdominal cavity AC through the opening SO. If, in this process, relative movement of the insertion part 10 and the endoscope inserting part 5 must be restricted, the endoscope lock button 47 is pressed and contacted against the endoscope inserting part 5 to fix the movement of the endoscope inserting part 5 by the frictional force. Since the endoscope lock button 47 is provided, the endoscope lock button 47 can be manipulated to restrain relative movement of the endoscope 3 with respect to the overtube 2, and the overtube 2 and the endoscope inserting part 5 can thus be inserted into the body simultaneously. Also, since the task of inserting the endoscope 3 can be performed while holding the proximal handle 44 of the overtube 2, an operation in which the insertion part 10 of the overtube 2 is supported by one hand of the operator and the proximal handle 44 is held by the other hand, is enabled, and the operability is thus more improved.

After positioning, a treating step (S70) of performing observation, incision, cell sampling, suturing, or any of other various treatments (medical procedures) is carried out. After performing the treatment, the overtube 2 and the endoscope 3 are removed from the opening SO of the stomach wall SW.

Figure 25:
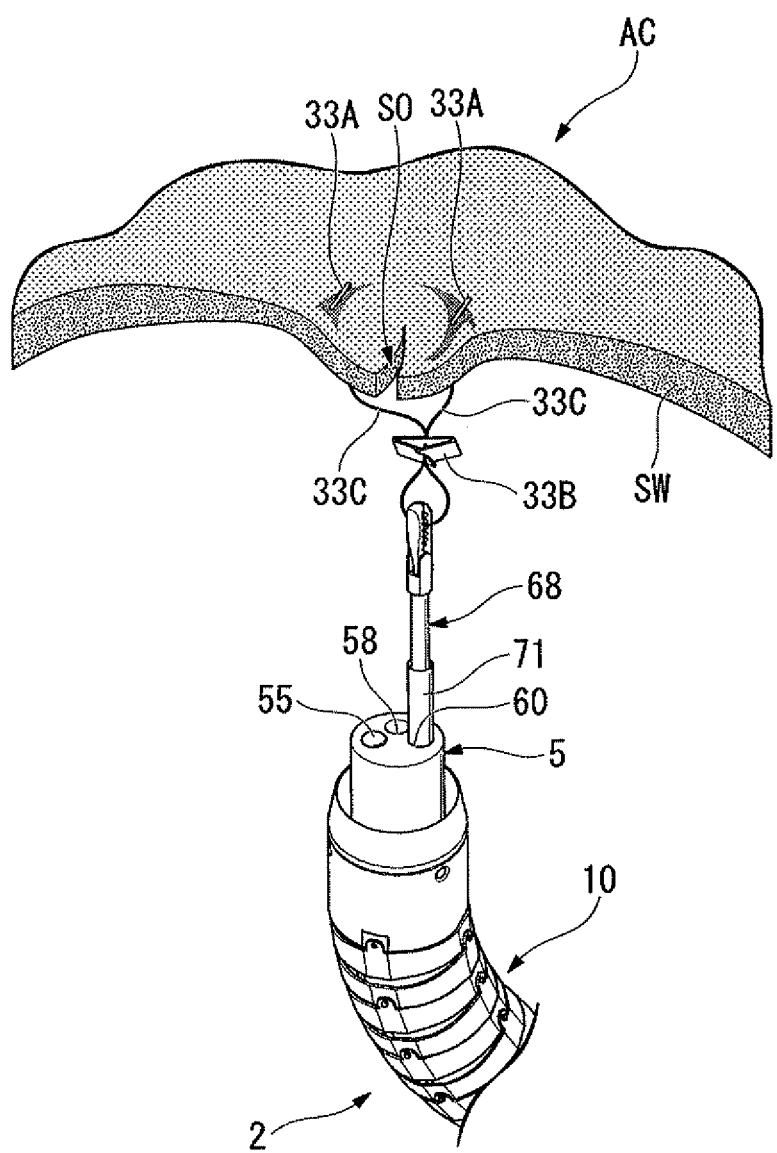
FIG. 25 is a view for describing the state of pulling and tensioning the suture of the placed double T-bars in the medical procedure according to the first embodiment.
Figure 26:
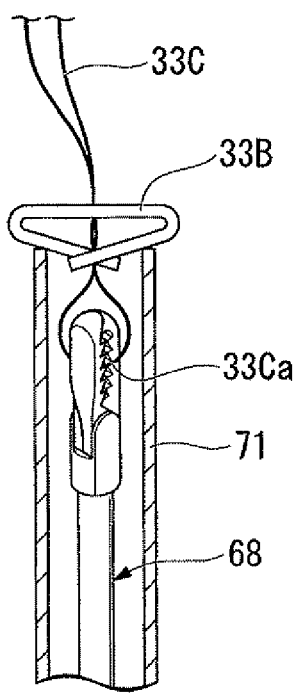
FIG. 26 is a view for describing the action in FIG. 25.
Figure 27:
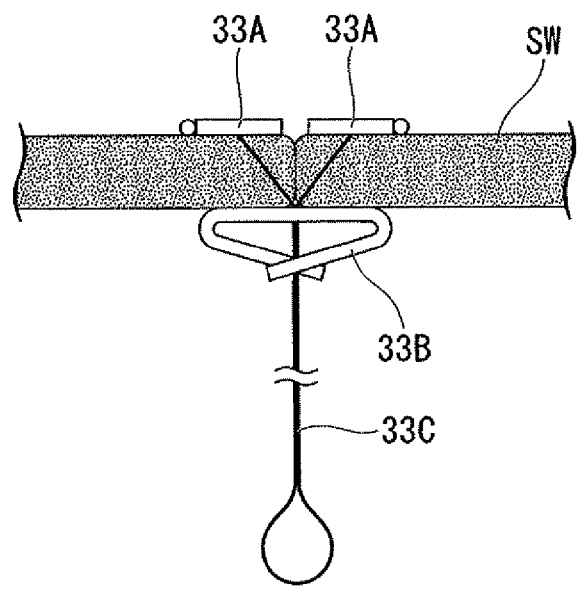
FIG. 27 is a view for describing the state of the stomach wall being bound with the double T-bars in the medical procedure according to the first embodiment.

In a suturing step (S80), when removing the endoscope 3 from the opening SO, as shown in FIG. 25, the grasping forceps 68 inserted to freely advance and retract in the outer sheath 32, are protruded with the outer sheath 32 from the treatment instrument insertion channel 60. Then, as shown in FIG. 26, the large diameter part 33Ca of the sutures 33C is held and pulled by the grasping forceps 68 while making the distal end of the outer sheath 32 abut the stopper 33B of the double T-bars 33, which had been placed in advance. Thus, as shown in FIG. 27, by moving the stopper 33B to clinch the stomach wall SW, the opening SO is thereby sutured. Additional double T-bars 33, etc., are provided to perform further suturing if necessary. In this process, since the insulation is performed in the process of placing the double T-bars 33 at the stomach wall SW, suturing by means of additional double T-bars 33 can be performed readily.

After suturing, the endoscope 3 and the overtube 2 are drawn out of the patient, the pressure applied to the abdominal cavity AC is released, and the surgical procedure is ended.

According to this overtube 2, since the gaps between the joint rings 13 are filled by the inner braid 16, when inserting the endoscope inserting part 5 in the lumen 7, the inner surface of the inner braid 16 serves as a guide so that the endoscope inserting part 5 can be advanced without becoming caught between the joint rings 13. When doing so, since the inner braid 16 is formed by braiding the thin metallic wire 30, deformation from both compression and pulling is possible. Also, when the bending tube 15 bends by the turning of the plurality of joint rings about the connecting shafts 12, the inner braid 16 suitably follows suit, so that it is possible to smoothly bend the bending tube 15.

When curving the bending part 8, by pulling the bending wire 11 toward the proximal side, the joint rings 13 turn at a predetermined angle about the connecting shafts 12 in the sequence in which the joint rings 13 are disposed from the distal end side. Thereby, it is possible to form the bending part 8 having a prescribed curve. On the other hand, to extend the bending part 8 to be straight, the bending wire 11 is loosened. At this time, due to the resiliency of the endoscope inserting part 5, the bent state is straightened. In accordance with this, the bending part 8 can also be straightened. Following this, incising of tissue can be more readily performed.

Second Embodiment

A second embodiment according to this invention shall now be described with reference to the drawings.

A point of difference of the second embodiment with respect to the first embodiment is that when a bending tube 73 of an overtube 72 according to this embodiment extends in a straight line manner, at least a portion of the peripheral edges of adjacent joint rings 75 overlap in the axial direction so as not to alter the inner diameter of the bending tube 73.

Figure 28:
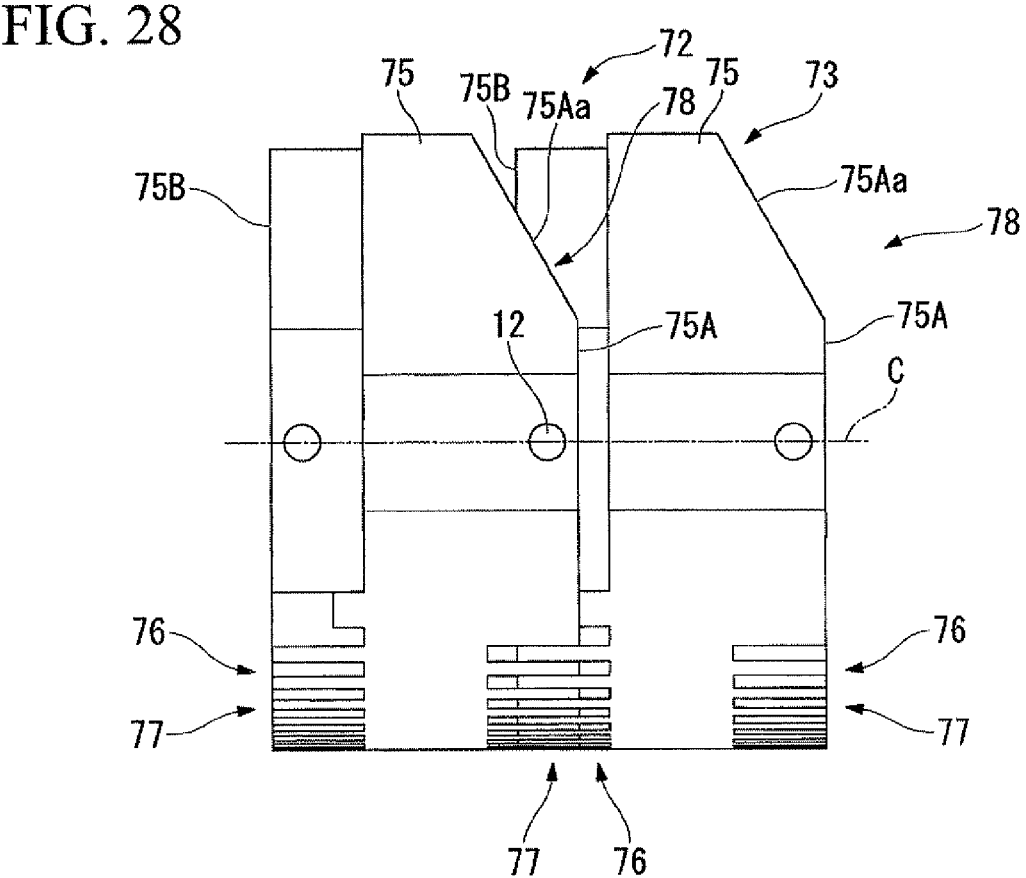
FIG. 28 is a view of the principal portions of an overtube according to the second embodiment.
Figure 29:
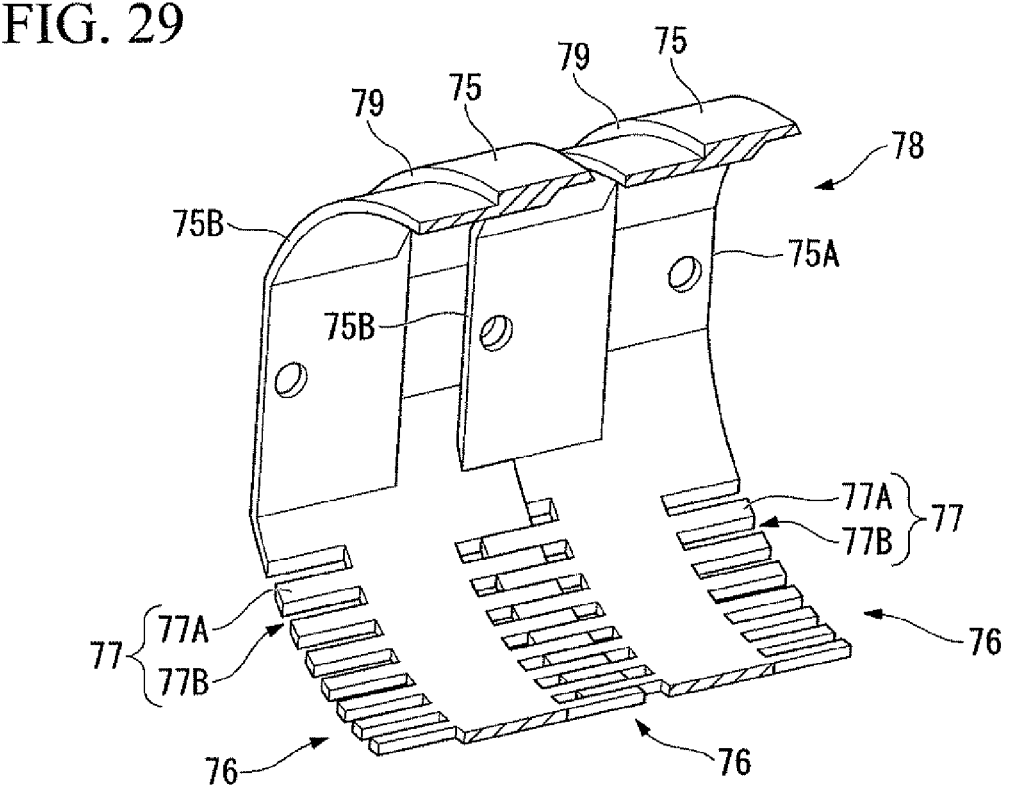
FIG. 29 is a perspective sectional view of the overtube according to the second embodiment.

As shown in FIG. 28 and FIG. 29, comb teeth 77 are provided at a specified interval in the circumferential direction in a partial region 76 of the peripheral portion of a proximal end surface 75A and a distal end surface 75B of each joint ring 75.

The comb teeth 77 consist of teeth 77A and slits 77B which are alternately provided so that the comb teeth 77 disposed on the adjacent proximal end surface 75A of the joint ring 75 and the distal end surface 75B of the opposing joint ring 75 mesh. The teeth 77A are of a length so that the meshing of the comb teeth 77 is maintained even when the proximal end surface 75A and a distal end surface 75B come apart by the curvature of the bending tube 15 at a predetermined angle.

In a separate region 78 in which the comb teeth 77 are not provided, a portion 75Aa of the proximal end surface 75A that becomes the inner side in the radial direction during curving is formed slanting with respect to the distal end surface 75B. In this region 78, a step 79 is formed so that the distal end surface 75B has a smaller diameter than the proximal end surface 75A by an amount corresponding to the wall thickness of the joint ring 75. Thereby, when the bending tube 15 bends, the distal end surface 75B of another joint ring 75 that is adjacent to the proximal end surface 75A of the joint ring 75 becomes fitted on the inner side.

Actions of the present embodiment shall now be described in line with a medical procedure performed via a natural orifice using the overtube 2 similarly to the first embodiment.

First, the inserting step (S10) is carried out similarly to the first embodiment.

Figure 30:
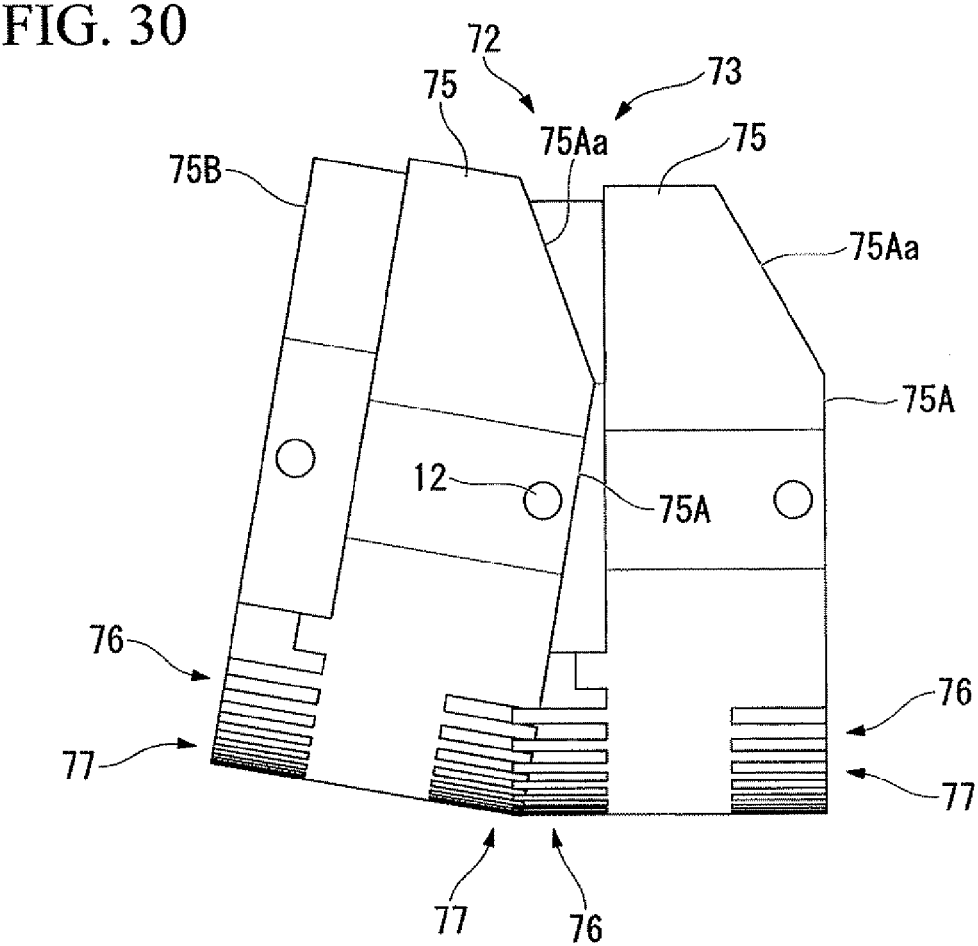
FIG. 30 is a view showing the action of the principal portions of the overtube according to the second embodiment.
Figure 31:
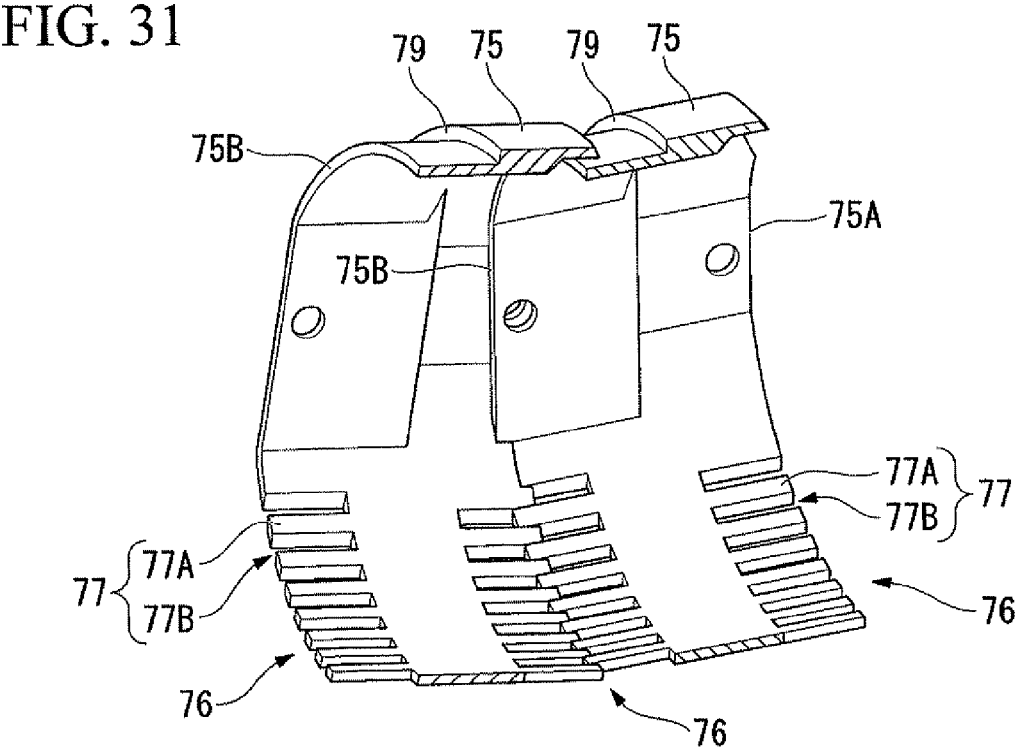
FIG. 31 is a perspective sectional view showing the action of the overtube according to the second embodiment.

Here, even when the bending tube 15 is bent, as shown in FIG. 30 and FIG. 31, the comb teeth 77 that are disposed on the distal end surface 75B of one joint ring 75 engage with the comb teeth 77 that are disposed on the distal end surface 75B of another joint ring 75 adjacent thereto. For this reason, gaps are not formed between the joint rings 75, and so when inserting the endoscope 3 in the overtube 2, even if the distal end thereof passes through the bending tube 73, the distal end of the endoscope inserting part 5 does not enter a gap between the joint rings 75. Accordingly the endoscope inserting part 5 moves smoothly in the lumen 7.

Afterward, the steps from the distending step (S20) to the suturing step (S80) are performed similarly to the first embodiment. After the surturing, the endoscope 3 is removed from the patient, the pressure applied to the abdominal cavity AC is released, and the surgical procedure is ended.

According to this overtube 2, since there are no gaps between the joint rings 75 regardless of whether there is bending or not, the endoscope inserting part 5 can be smoothly inserted into the insertion part 10 similarly to the first embodiment. Also, since there is no inner braid 16 such as that of the overtube 2 according to the first embodiment, it is possible to secure a lumen with a greater diameter than the diameter of the lumen according to the first embodiment.

Through in the above embodiment, a flexible endoscope is used as an observation device, this invention is not limited thereto and, for example, a so-called capsule endoscope may be placed inside the body, and while observing the interior of the body using the endoscope, an insertion part of a treatment device that does not have an observation device may be inserted through the overtube to perform the desired surgical procedure.

Figure 32:
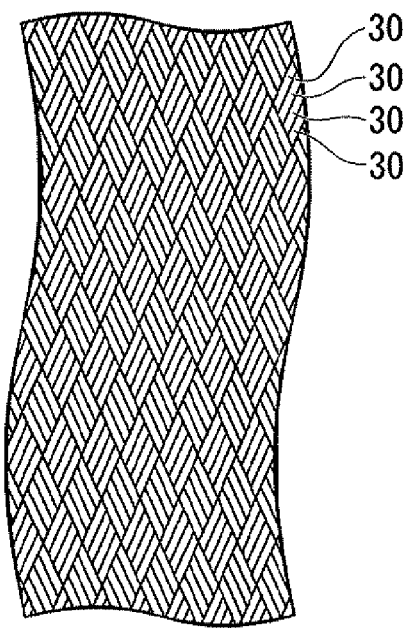
FIG. 32 is a view showing the constitution according to a modification example of the overtube according to the first embodiment.

Also, in the first embodiment, the inner braid 16 and the outer braid 17 are formed by braiding one thin metallic wire 30 so as to intersect with the central axis C of the lumen 7, but are not limited thereto. For example, as shown in FIG. 32, a plurality of the thin metallic wires 30 may be braided in a similar direction. In this case, although the movement angle is further constrained than in the case of a single wire, the strength is increased, and the required rigidity can be ensured. Also, by filling resin between the thin metallic wires 30, airtightness and watertightness may be ensured. Also, the thin wires may be a nonmetal instead of metal. Also, the surface of the thin metallic wires 30 or the entire inner braid may be coated with a resin or ceramics.

Figure 33:
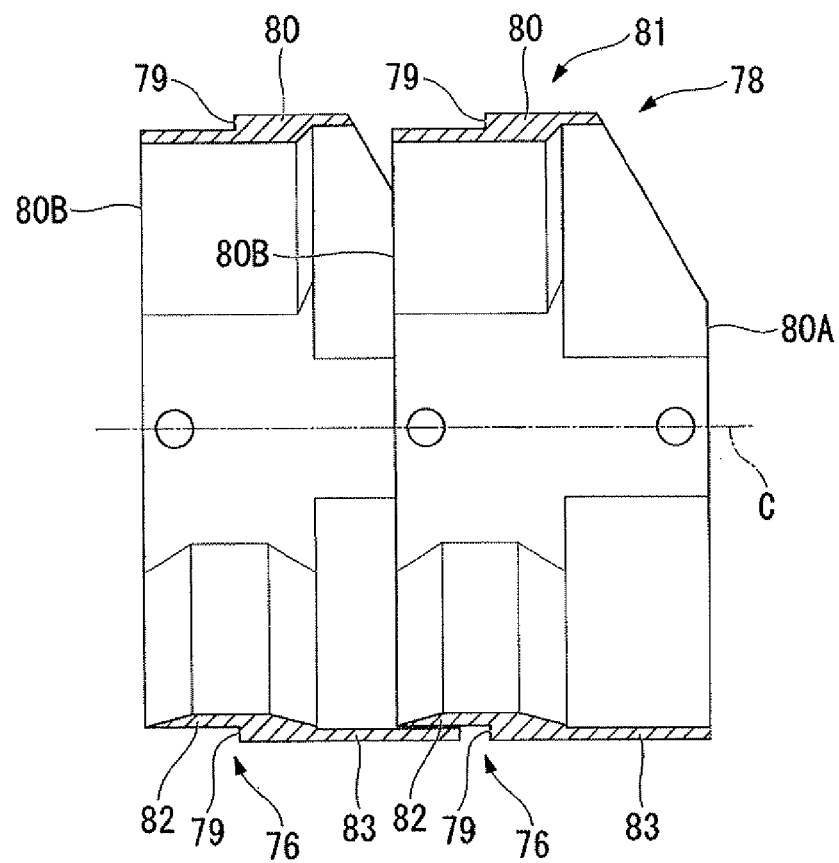
FIG. 33 is a view showing the principal portions of a modification example of the overtube according to the second embodiment.
Figure 34:
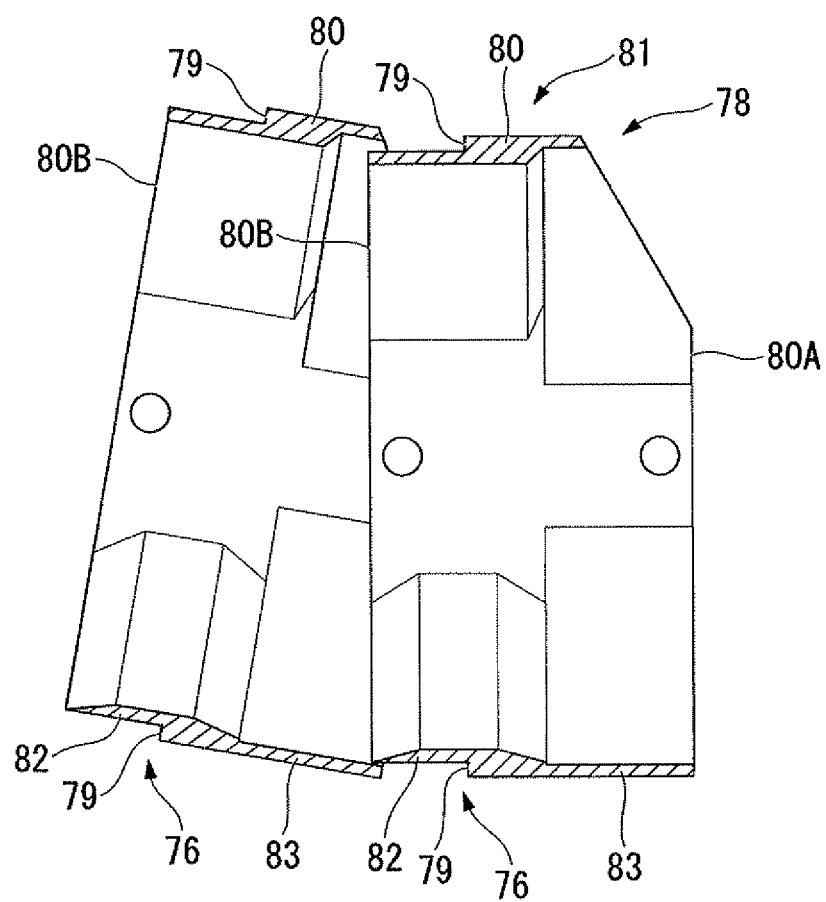
FIG. 34 is a view showing the action of the principal portions of the overtube according to the second embodiment.

Also, in the second embodiment, as shown in FIG. 33, a bending tube 81 may be constituted by a part of adjacent joint rings 80 overlapping in the radial direction of the joint rings 80. In this case, in the partial region 76 of the joint ring 75, the step 79 similar to the separate region 78 may be provided instead of the comb teeth 77 provided in the partial region 76 of the joint ring 75. That is, the joint ring 80 is provided with a small diameter part 82 of the distal end side and a large diameter part 83 on the proximal end side that fits with the small diameter part 82 of the adjacent joint ring 80. Here, as shown in FIG. 34, the length of the small diameter part 82 and the large diameter part 83 along the central axis C is a length that is capable of maintaining the mutual fitting so that gaps are not formed between the joint rings 80 even when the bending tube bends at a predetermined curvature. Accordingly, when inserting the endoscope 3 in the overtube 2, even if the distal end thereof passes through the bending tube 81, the distal end of the endoscope inserting part 5 does not enter a gap between the joint rings 80.

Third Embodiment

An overtube according to this embodiment can bend the bending part and fix the bending state of the bending part with a single handle.

Figure 35:
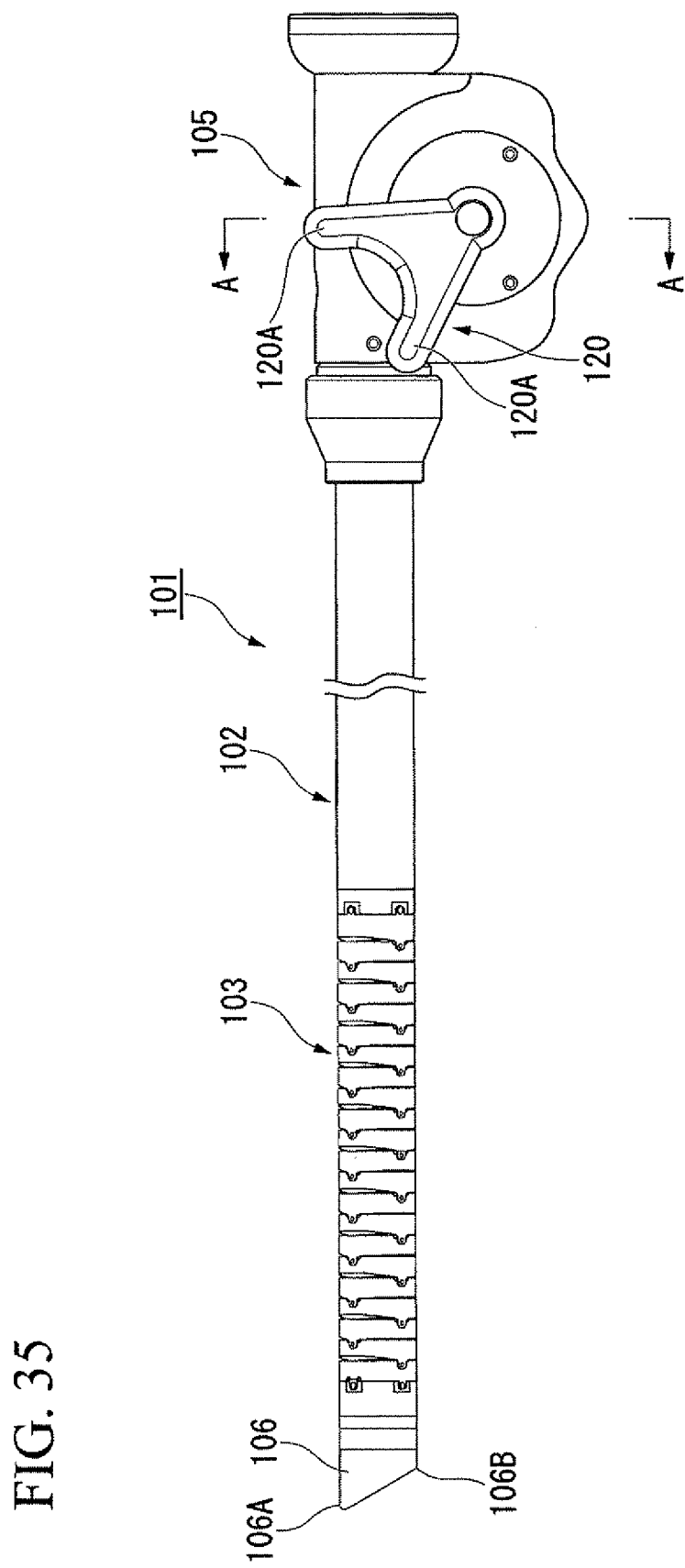
FIG. 35 is a view of an overtube according to the third embodiment.

FIG. 35 shows an overtube 101 which is a medical instrument according to the present embodiment. The basic structure of the overtube 101 is the same as that of the overtubes of respective embodiments described above and includes: an insertion part 102 having a bending part 103; a wire 104 (described below) for bending the bending part 103; and a manipulating part 105 for manipulating the wire 104. In several figures including FIG. 35, an outer skin 112 described below is omitted in order to easily see the structure of the bending part 103.

A soft member 106 is attached to the distal end of the insertion part 102. The soft member 106 is made of a material such as rubber and prevents the tissue from being damaged by the distal end of the overtube 101 when inserting the overtube 101 into the body cavity. The distal end of the soft member 106 is cut so as to incline with respect to the axis of the insertion part 102 so that a first end part 106A which is drawn toward the proximal side by the wire 104 at the time of bending has a length in the axial direction longer than that of a second end part 106B opposite to the first end part 106 A.

Figure 36:
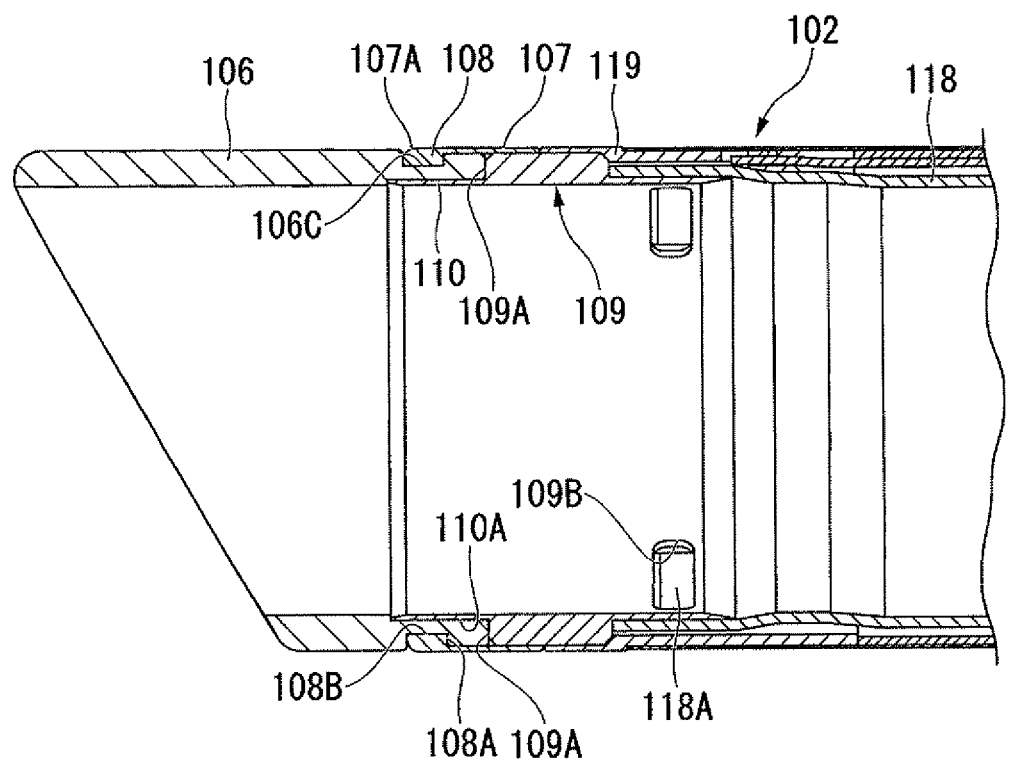
FIG. 36 is an enlarged sectional view of the distal end of the insertion part of the overtube.

FIG. 36 is an enlarged sectional view of the distal end of the insertion part 102. A groove 106C is provided on the outer surface of the proximal side of the soft member 106 along the circumference direction. The soft member 106 is fixed to the distal end of the insertion part 102 by a first fixing member 107 including a fitting part 108 which is capable of fitting to the groove 106C and a second fixing member 109 including a small diameter part 110 provided in the distal side thereof.

The soft member 106 is fixed as follows. Firstly, the proximal side of the soft member 106 is deformed to be inserted into the first fixing member 107 so that the groove 106C engages with the fitting part 108. Next, the second fixing member 109 is screwed to the soft member 106 from the proximal side of the first fixing member 107 so that a step 109A at the proximal side of the small diameter part 110 comes into contact with the back end of the soft member 106. As a result, in the axial direction, the soft member 106 is sandwiched between a proximal end surface 108S of the fitting part 108 and the step 109A of the second fixing member 109 and fixed thereto, and, in the radial direction, the soft member 106 is sandwiched between an inner surface 108B of the fitting part 108 and an outer surface 110A of the small diameter part 110 and fixed thereto. Therefore, the soft member 106 is securely fixed to the distal end of the insertion part 102.

When the soft member 106 is fixed, the distal end of the second fixing member 109 is positioned closer to the front side, that is, the distal end of the insertion part 102, than the distal end of the first fixing member 107. Therefore, even when the outer surface of the soft member 106 is pushed, since the portion of the soft member 106 where the groove 106C is provided is hardly deformed inward in the radial direction, the distal end of the first fixing member 107 is hardly exposed, thereby preventing the distal end of the first fixing member 107 from damaging the tissue. Furthermore, since an outer surface 107A of the distal side of the first fixing member 107 is formed as a curved surface, even when the distal end of the first fixing member 107 is exposed due to deformation of the soft member 106, the tissue is hardly damaged.

Figure 37:
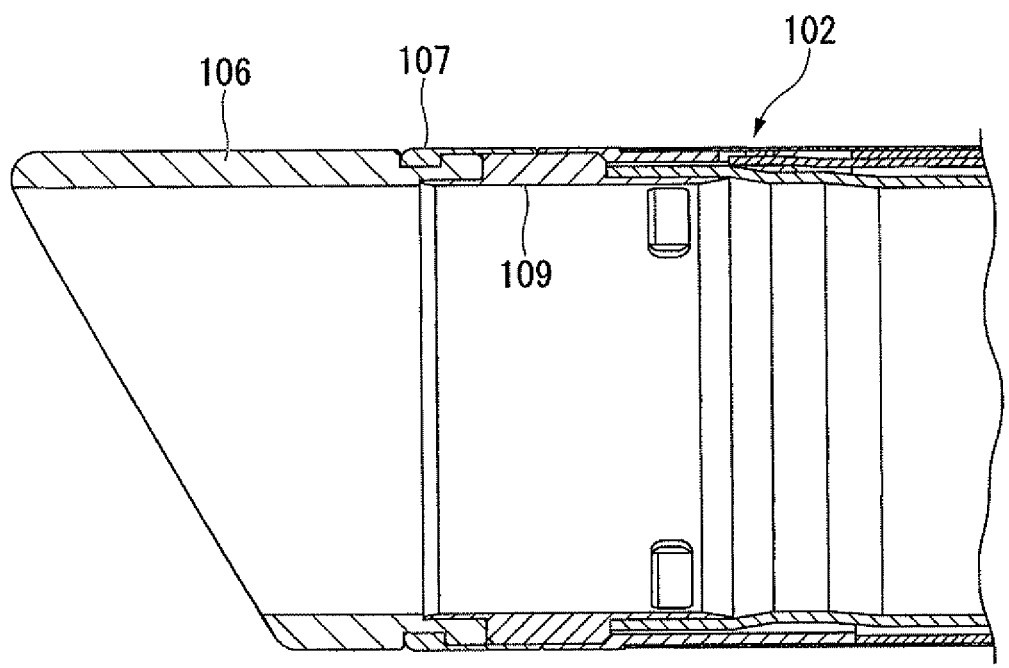
FIG. 37 is an enlarged sectional view of a modification example of the distal end of the insertion part of the overtube.

As shown in FIG. 37, dimensions or the like of the respective members may be set such that the distal end of the second fixing member 109 is positioned closer to the back side than the distal end of the first fixing member 107. In this case, since a portion of the soft member 106 positioned closer to the front side than the distal end of the second fixing member 109 is hardly deformed outward in the radial direction, the exposure of the distal end of the second fixing member 109 to the inner cavity of the insertion part 102 can be prevented. Since a device such as an endoscope can be inserted without becoming caught by the second fixing member 109 or the like, damage to the device can be prevented and the advancing and retracting manipulation of the device can be smoothly performed. Any of the configurations can be appropriately selected in response to an inserted device such as an endoscope.

Figure 38:
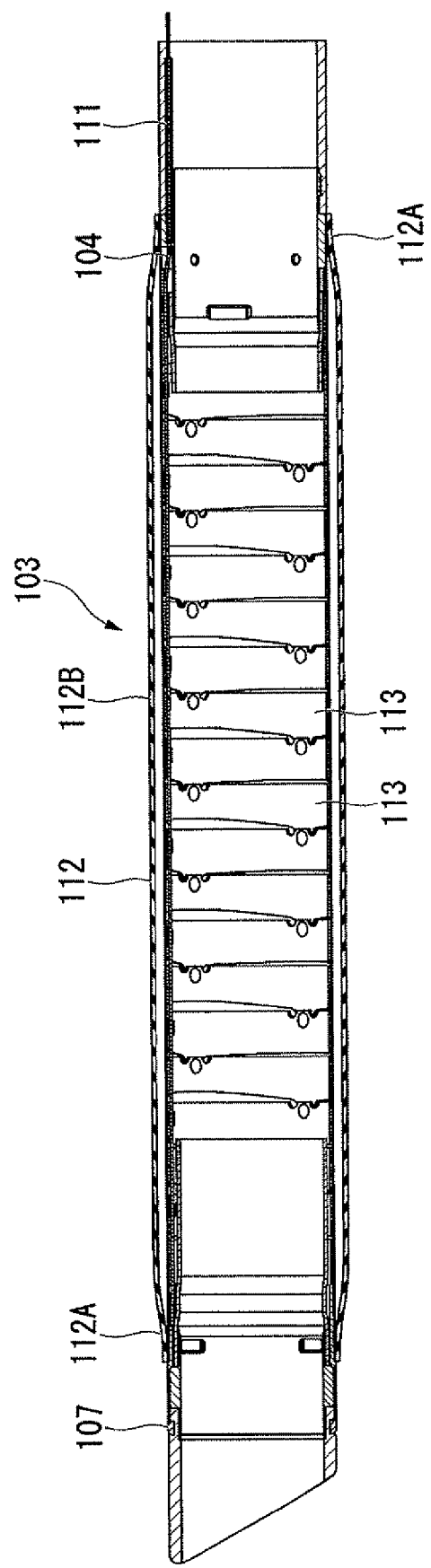
FIG. 38 is a sectional view of the bending part of the overtube.

FIG. 38 is a sectional view of the bending part 103. The wire 104 for manipulating the bending part 103 is made of so-called high-tension wire whose strength is enhanced by heat treatment or the like. Therefore, when manipulating, an accident such as the breaking of the wire 104 hardly occurs while making the diameter of the wire 104 small so as to keep the inner diameter of the insertion part 102 large. The surface of the wire 104 is coated with polytetrafluoroethylene (PTFE) so as to reduce the friction between a coil tube 111 and the wire 104 or the friction between an insertion tube 116 (described below) attached to the joint ring 113 and wire 104, thereby efficiently transmitting the force added to the wire 104. Therefore, since the amount of the force added to the wire 104 becomes smaller, a wire having a smaller diameter can be used. As a result, the inner diameter of the insertion part 102 can be enlarged. A defric coat, silicon oil, or the like may be used for reducing the friction instead of PTFE.

Figure 39:
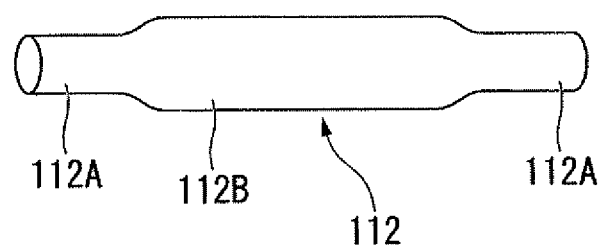
FIG. 39 is a view of a shape of the outer skin.

The outer skin 112 that constitutes the outermost layer of the bending part 103 is made of a polyurethane tube having a thickness of about 0.1 mm. As shown in FIG. 39, diameters of end portions 112A in the axial direction of the outer skin 112 are substantially equal to that of the first fixing member 107 or the like. A diameter of a medium portion 112B which is sandwiched between the end portions 112A is greater than that of the end portion 112A by several mm. Accordingly, both end portions 112A are attached closely and reliably bonded to the first fixing member 107 or the like. The medium portion 112B covers the outside of the joint rings 113 and suitably prevents the tissue from being damaged due to the joint rings 113 while allowing movement of the joint rings 113 accompanying with bending.

Figure 40:
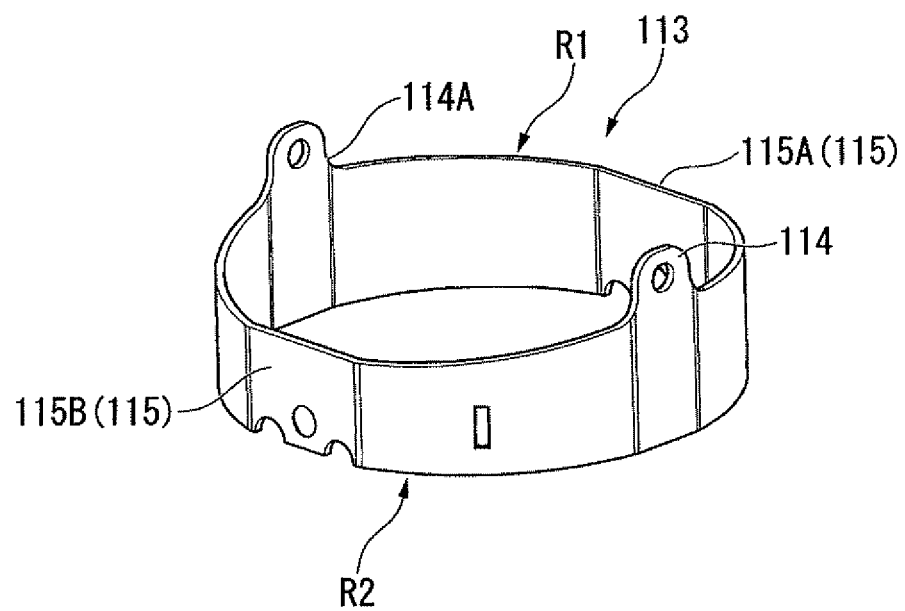
FIG. 40 is a perspective view of the joint ring of the bending part.
Figure 41:
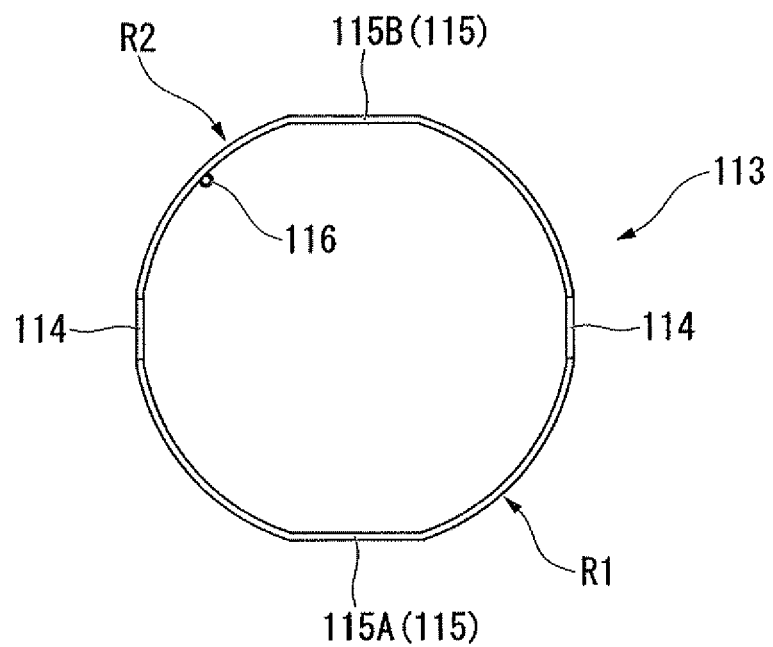
FIG. 41 is a view of the joint ring seen from the axial direction.

FIG. 40 shows the joint ring 113 that is attached to the bending part 103. The join ring 113 is made of metal having a thickness of about 0.3 mm in order to ensure the inner diameter of the bending part 103 as large as possible. As shown in FIG. 41 the joint ring 113 is formed such that a shape seen from the axial direction is as equal to circular shape as possible. That is, in the joint ring 113, while a connecting part 114 which is connected to the distal side joint ring and a connected part 115 which is connected to the proximal side joint ring are formed as a plane shape, the other portions are substantially formed as an arc shape around the axis of the joint ring 113. A base portion 114A which is a portion of the connecting part 114 protruding in the axial direction is formed as a curved shape in order to prevent concentration of the stress. End portions of the planar connecting part 114 in the circumferential direction are formed so as to contact with the base portion 114A at the end surface of the distal side of the joint ring 113. The base portion 114A may be partly formed in a line shape as long as the base portion 114A is substantially formed in a curved shape so as not to have a corner at which the stress concentrates. By forming thus, the joint ring 113 having sufficient strength can be formed while the joint ring 113 is formed of a thin metal.

The smaller the areas of the planar connecting part 114 and connected part 115 become, the more circular the shape of the joint ring 113 in the radial direction becomes such that the joint ring 113 has a larger inner cavity. Therefore, it is preferable that the sizes of the connecting part 114 and connected part 115 in the circumference direction of the joint ring be set as small as the strength necessary for connecting can be maintained. In this embodiment, the width of the connecting part 114 is set to 2.5 mm and a diameter of an inscribed circle of the joint ring 113 (substantially equal to the effective inner diameter of the bending part 103) is set to 15.7 mm.

An end surface of the proximal side of the joint ring 113 is a cross section orthogonal to the axis of the joint ring 113. However, in the case of two connected parts 115, one connected part (first connected part) 115A has a length in the axial direction longer than the other connected part (second connected part) 115B so as to protrude toward the front side in the axial direction than the second connected part 115B. Therefore, an area of an outer peripheral surface of a first region R1 which is a region between the connecting parts 114 of the connected part 11 SA side is larger than that of a second region R2 which is a region between the connecting parts 114 of the second connected part 115B side.

Figure 42:
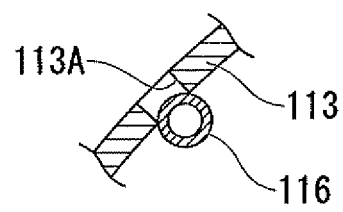
FIG. 42 is an enlarged sectional view of an insertion tube provided in the joint ring.

The insertion tube 116 into which the wire 104 is inserted at the each joint ring 113 is attached to the inner surface of the joint ring 113 at a position on the inner surface substantially central with respect to the connecting part 114 and the second connected part 115B. As enlargedly shown in FIG. 42, the insertion tube 116 is attached by laser welding, soldering, or the like with the outer peripheral surface of the insertion tube 116 partly buried in a hole 113A provided at the joint ring 113. Accordingly the inner peripheral surface of the insertion tube 116 is arranged so as to be tangent to the virtual inner peripheral surface of the joint ring 113 at the hole 113A such that the inner surface of the joint ring 113 flatly connects with the inner surface of the insertion tube 116 without a step. Therefore, the wire 104 can be smoothly advanced and retracted and the bending part 103 can maintain a larger inner cavity. A recessed portion which does not penetrate the joint ring 113 may be provided at the inner surface of the joint 113 instead of the hole 113A of the joint ring 113.

Figure 43:
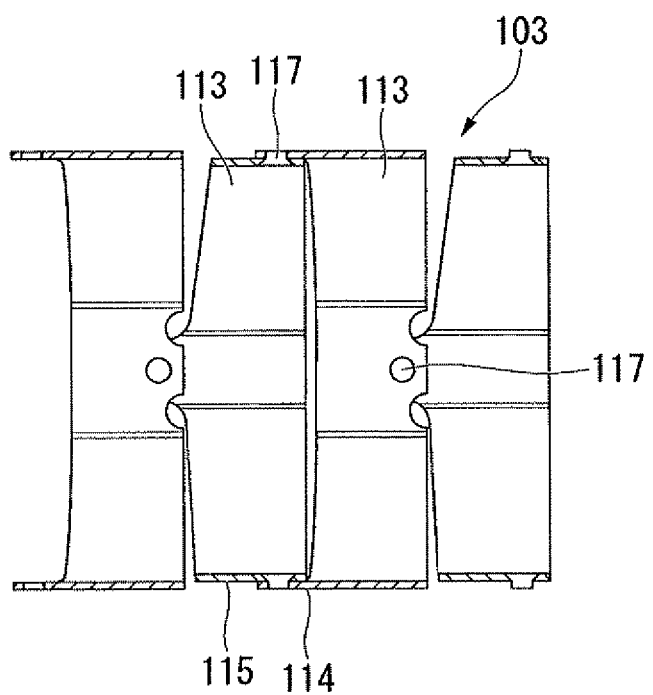
FIG. 43 is a sectional view showing the connecting state of the joint rings.
Figure 44:
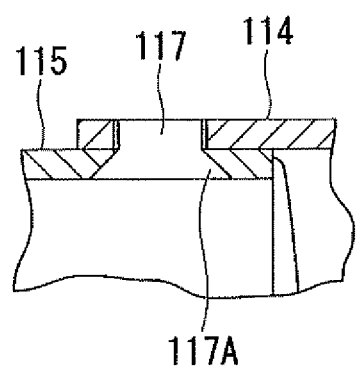
FIG. 44 is a sectional view showing the connecting state of the joint rings.

FIGS. 43 and 44 are enlarged sectional views of the connecting portion of the joint ring 113. The inner side of the connected part 115 in the radial direction is connected to the outer side of the connecting part 114 in the radial direction by a plate pin 117 having a truncated-cone shaped flange 117A. The plate pin 117 is inserted from the connected part 115. The distal end of the plate pin 117 is inserted into the connecting part 114 and is integrally fixed to the connecting part 114 by laser welding. A hole provided in the connected part 115 has a shape matching the flange 117A of the plate pin 117 so that the flange 117A is housed within the hole. Therefore, the flange 117A does not protrude toward the inner cavity of the bending part 103. Since the flange 117A does not protrude toward the outside or inside of the bending part 103, the outer and inner surfaces of the bending part 103 can be formed smoothly. As a result, the bending part 103 can easily be inserted into the body cavity and a device such as an endoscope which is inserted into the overtube 101 can be smoothly advanced and retracted. Furthermore, it is possible to secure the insertion part 102 with a greater inner diameter while keeping the outer diameter of the insertion part 102 small.

Figure 45:
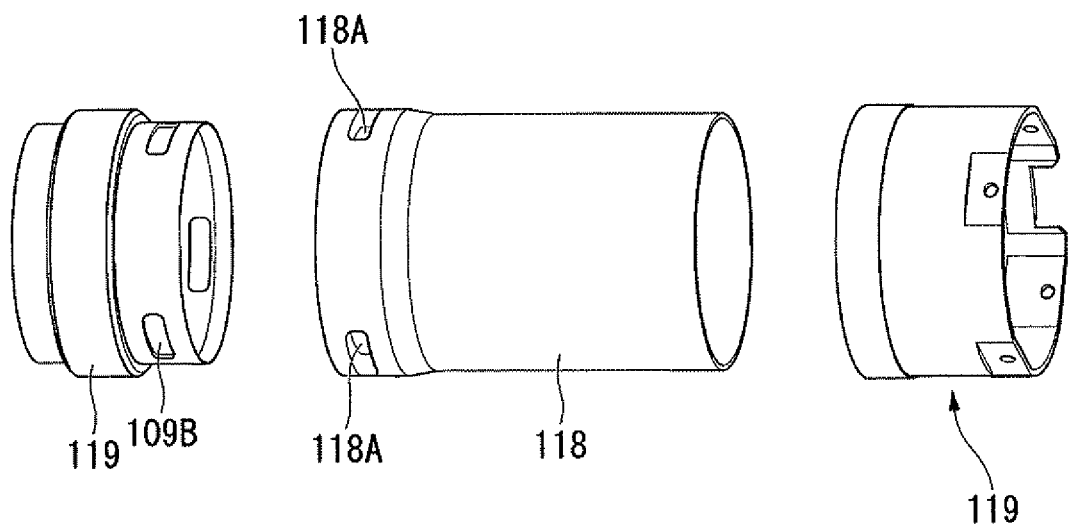
FIG. 45 is a view showing the fixing state of a blade of the overtube.

A blade 118 which covers the inside of the joint ring 113 is formed by knitting a strand made of resin. FIG. 45 shows the attachment state of the blade 118. The distal side of the blade 118 is transformed by means of heat and provided with a plurality of protrusions 118 protruding inward. As shown in FIG. 36, the distal side of the blade 118 is attached to the second fixing member 109 so as to cover the proximal end of the second fixing member 109 from the outside with the protrusions 118A fitted to holes 109B which is provided in the proximal side of the second fixing member. Furthermore, a third fixing member 119 is screwed with respect to the second fixing member 109 and fixed thereto so as to cover the outside of the blade 118. By joining in this manner, when the blade 118 extends in the axial direction, the blade 118 can be prevented from falling in virtue of a fitting of the protrusion 118A to the hole 109B of the second fixing member 109. When the blade 118 is compressed in the axial direction, in virtue of the third fixing member 119, the fitting of the protrusion 118A to the hole 109B of the second fixing member 109 is not broken, thereby preventing separation of the blade 118 from the second fixing member 109. Therefore, these two materials can be securely connected to each other without increasing the thickness of the connecting portion of the blade 118. A recessed portion having a predetermined depth may be provided instead of the hole 109B of the second fixing member 109.

Figure 46:
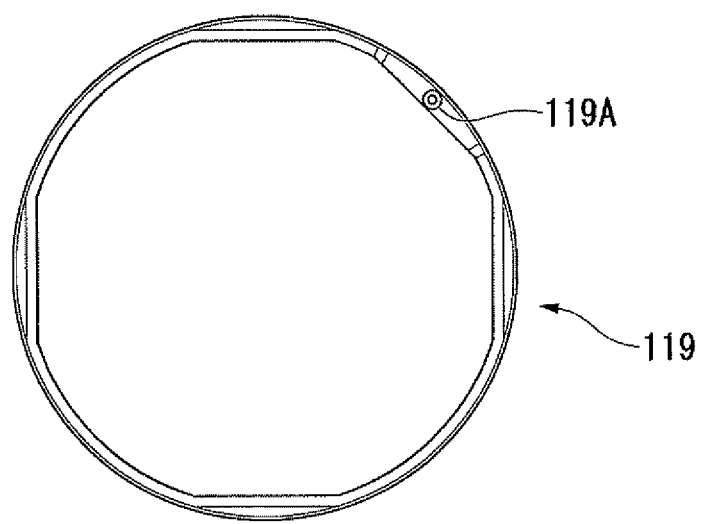
FIG. 46 is a view of a third fixing member of the overtube.

The distal end of the wire 104 which has been inserted into the insertion tubes 116 of the joint rings 113 is fixed to the third fixing member 119. As shown in FIG. 46, in the third fixing member 119, a wire fixing part 119A to which the wire 104 is fixed is formed to be thicker than the other parts. The wire 104 is inserted into the wire fixing part 119A and fixed thereto by soldering or the like. By adjusting the thickness of the wire fixing part 119A or the like so that the diameter of the inscribed circle of the third fixing member 119 is not smaller than that of the inscribed circle of the joint ring 113, the wire 104 can be fixed without changing the effective inner diameter of the bending part 103. Furthermore, since the axis of the inscribed circle of the third fixing member 119 can be maintained substantially coaxial with that of the inscribed circle of the joint ring 113, insertion ability of a device such as an endoscope is enhanced as compared with the case where the wire fixing part 119A is provided so as toward protrude to the inner cavity.

A portion of the insertion part 102 which is positioned closer to the proximal side than the bending part 103 is formed of a urethane tube having a coil therein. The inner surface of the insertion part 102 is coated with hydrophilic polymer or the like (not shown) and is lubricated by supplying water from a port 128 (described below) to the inner cavity thereof, thereby improving the manipulation of advancing and retracting of an endoscope.

Figure 47:
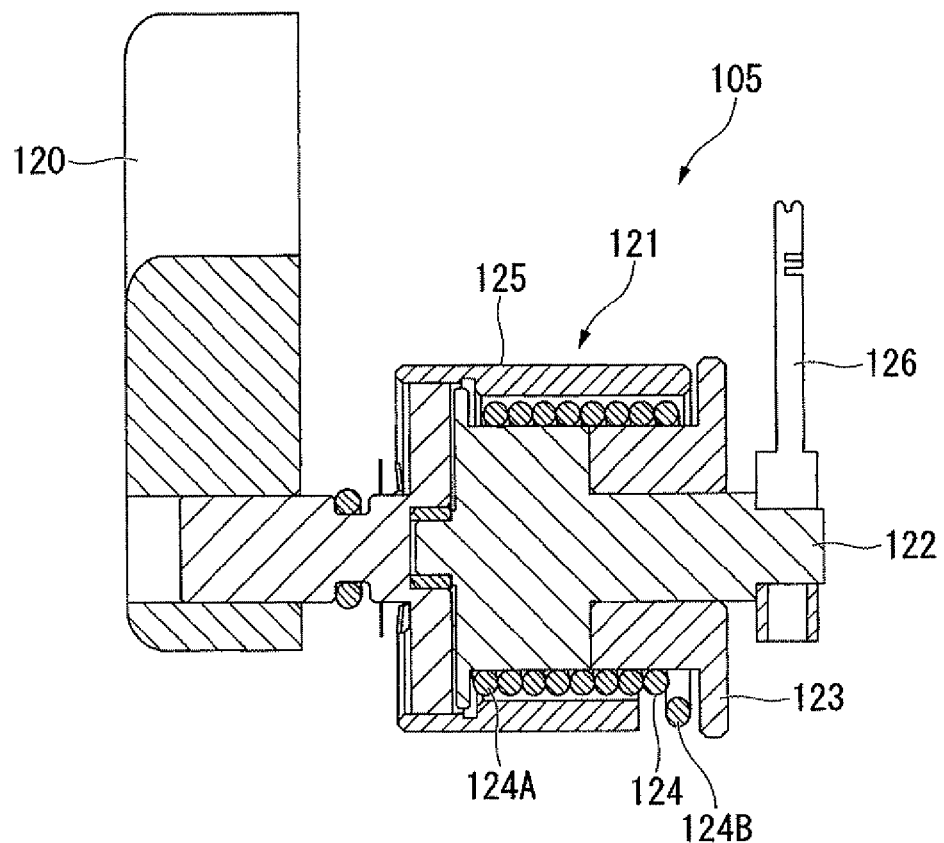
FIG. 47 is a sectional view taken along line A-A of FIG. 35 and showing the principal portions of the manipulating part of the overtube.

FIG. 47 is a sectional view taken along line A-A of FIG. 35. Note that FIG. 47 shows only the principal portions of the manipulating part 105 for the following illustration. A handle 120 for manipulating the wire 104 is provided in the manipulating part 105. As shown in FIG. 35, a plurality of protrusions 120A is provided in the handle 120. Therefore, even when the handle 120 rotates by manipulation, the handle 120 can always be easily manipulated with one hand by using the protrusion 120A in the position where a manipulation can be performed easier.

A one-way clutch 121 which holds the bending part 103 at an arbitrary bending amount is provided in the manipulating part 105. As shown in figures, the one-way clutch 121 includes: a drive shaft 122; a bearing 123 into which the drive shaft 122 is inserted; a spring 124 which is twisted on the outer surfaces of the drive shaft 122 and the bearing 123; and a cover 125 which is provided so as to cover the spring 124.

The handle 120 is attached to one end of the drive shaft 122. A pulley 126 which is connected to the wire 104 is attached to the other end of the drive shaft 122. The spring 124 is twisted clockwise toward the pulley 126 as seen from the handle 120 side. A first end part 124A of the spring 124 closer to the handle 120 is engaged with the drive shaft 122 and a second end part 124B closer to the pulley 126 comes into contact with the cover 125. The cover 125 is attached to the handle 120 such that the cover 125 and the handle 120 rotate together. The bearing 123 is fixed to the other portion of the manipulating part 105 so as not to rotate. Movement of the one-way clutch 121 at the time of using will be described below.

Figure 48:
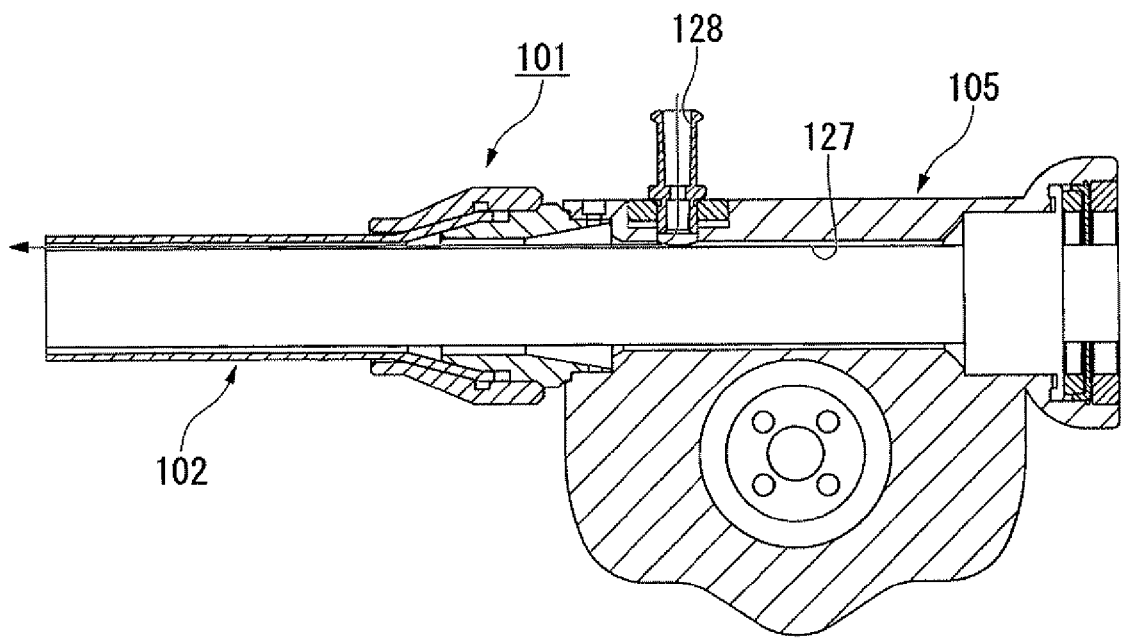
FIG. 48 is a sectional view of the manipulating part of the overtube.

As shown in FIG. 48 as a cross section, the port 128 for feeding air and water is provided in a duct 127 which is provided inside the manipulating part 105 and connected with the inner cavity of the insertion part 102. A three way stopcock (not shown) is air-tightly attached to the port 128 so that the port 128 selectability supplies carbon dioxide for aeroperitoneum or water for damping the above-described hydrophilic coating to the inner cavity of the insertion part 102 if necessary. Since the inner diameter of the overtube 101 is larger than that of a standard endoscopic channel for feeding air, influence such as resist of the duct is reduced. Accordingly, control of the pneumoperitoneal pressure can be performed with higher accuracy. Furthermore, since water is fed from the port 128, even when an endoscope is inserted from the proximal end of the duct 127, water can be additionally fed in order to damp the hydrophilic coating.

Since the proximal end of the wire 104 is drawn from a hole (not shown) provided at the inner surface of the duct 127 to the outside of the duct 127 to be fixed to the pulley 126 of the manipulating part 105, there is no large step with which a device such as an endoscope is hooked in the inner surface of the duct 127. Therefore, a device such as an endoscope is hardly caught. In order that the wire 104 can bend to some extent in the all direction so as to accompany with the shape of the body cavity when inserting the overtube 101, the wire 104 is fixed to the pulley 126 with the wire slightly slack in a state where the bending part 103 does not bend.

Movement of the overtube 101 constituted as above described at the time of use is described as follows.

When inserting the distal end of the insertion part 102 into the body cavity, the bending part 103 is made to be in a non-bending state in which the bending part 103 is substantially straight. In this state, since the wire 104 is attached with the wire in a slack state, the wire 104 and the bending part 103 can be inserted into the body cavity while the bending part 103 accompanies with the wire 104 even when the body cavity curves to some extent.

Figure 49:
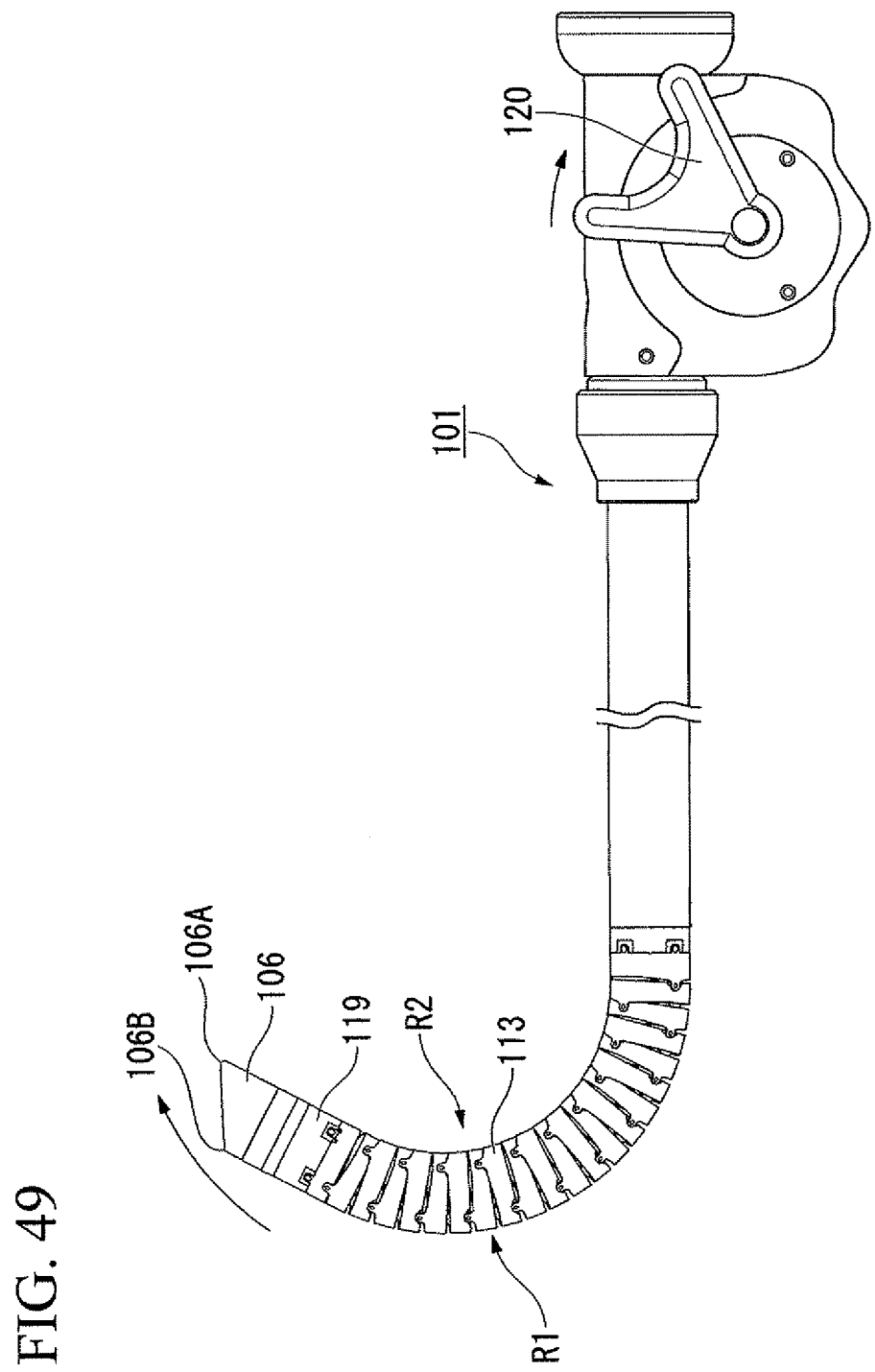
FIG. 49 is a view showing the bending state of the overtube.

When bending the bending part 103 by manipulation of the manipulating part 105, as shown in FIG. 49, the handle 120 is rotated clockwise, that is, toward the proximal side. Then the wire 104 which is connected to the pulley 126 is drawn toward the proximal side and the third fixing member 119 which is connected to the distal end of the wire 104 is moved toward the proximal side, thereby bending the bending part 103 corresponding to a manipulation amount of the handle 120.

At this time, since the insertion tube 116 into which the wire 104 is inserted is provided at the second region R2 of the respective joint ring 113, the bending part 103 is transformed such that the second region R2 is positioned inside a loop which is formed by bending. Since the first region R1 of the respective joint ring 113 which is positioned outside the loop is formed to have a surface area larger than the second region R2, a gap between the joint rings 113 is not large even in the outside of the loop. Therefore, it is possible to prevent the blade 118 or the like from getting caught in the gap to form a step which resists the advancing and retracting manipulation of an inserted device such as an endoscope.

Since the blade 118 is made of resin, even when an accident such as the rupture of the strand occurs, the distal end of the strand does not protrude from the gap between the joint rings 113 so as to stave in the outer skin 112. As a result, damage of the tissue or the like can be suppressed as compared with a blade made of metal.

Furthermore, as shown in FIG. 49, since the soft member 106 is attached such that the second end part 106B whose length in the axis direction is shorter is positioned in the outside of the loop formed by the bending of the bending part 103, the distal end surface of the soft member 106 tends to contact with the inner wall of the body cavity or the like with the angle therebetween being relatively small. Therefore, the overtube 101 is hardly caught by the body cavity and can be smoothly inserted into the body cavity.

When bending the bending part 103, the force acts on the pulley 126 of the manipulating part 105 to rotate the pulley 126 toward the distal side due to the tensile force of the wire 106. However, when a tendency for the pulley 126 to rotate toward the distal side arises, the drive shaft 122 is rotated together with the pulley 126 and then the first end part 124A of the spring 124 which is engaged with the drive shaft 122 is rotated together with the drive shaft 122. As a result, since the spring 124 fastens the drive shaft 122 and the bearing 123 fixed to the manipulating part 105 in a unitary manner, the pulley 126 cannot be rotated (see FIG. 47). Therefore, even when the operator manipulates the handle 120 to obtain a predetermined bending amount and then unclasps the handle 120, the bending state of the bending part 103 is maintained, thereby enabling the manipulation easily.

When making the bending amount of the bending part 103 small, the operator rotates the handle 120 counterclockwise. At this time, the loop of the spring 124 is loosened by means of the cover 125 which is moved together with the handle 120 since the second end part 124B of the spring 124 is rotated counterclockwise, that is, toward the distal side, together with the cover 125. As a result, the drive shaft 122 can rotate relative to the bearing 123, thereby performing the manipulation without any resistance.

By operating the one-way clutch 121 in the above-described manner, the operator can always perform the manipulation of the bending part 103 by the manipulating part 105 without any resistance, Furthermore, even when the operator unclasps the handle 120 in an arbitrary state, it is possible to maintain a state of the bending part 103 where the operator has clasped the handle 120. When the bending part 103 is not bent, the form of the bending part 103 is not maintained since the wire 104 is slack.

The scope of the art of this invention is not restricted to the embodiments described above, and various changes can be added within a range that does not fall outside the spirit of this invention.

Figure 50:
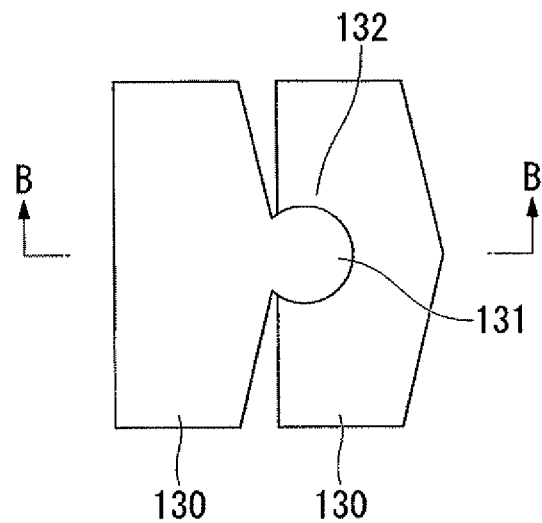
FIG. 50 is a view showing the connecting state of the joint rings of the overtube according to a modification example of the third embodiment.
Figure 51:
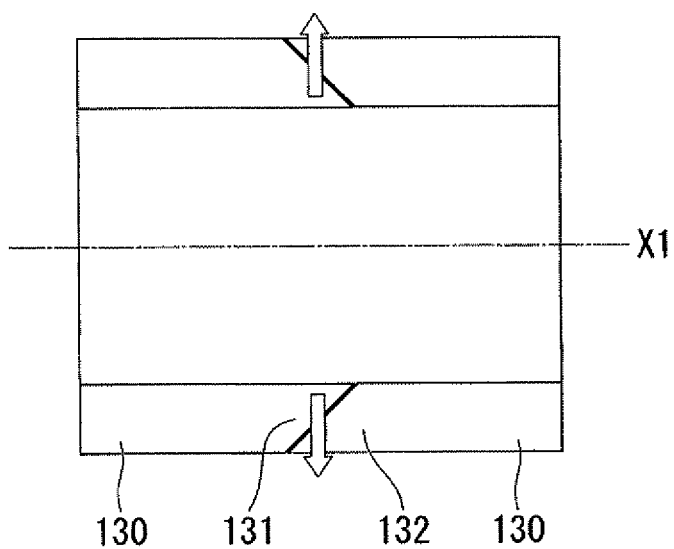
FIG. 51 is a sectional view taken along line B-B of FIG. 50.

Though in the above embodiment, the joint rings 113 are connected to each other by the plate pin 117, instead of the plate pin 117, for example, a connecting part 131 may be formed in a substantially truncated-cone shape and a connected part 132 may be formed in a shape which matches the connecting part 131 such that the joint rings 130 are connected to each other without using a plate pin by engaging the connecting part 131 with the connected part 132 inwardly in the radial direction as shown in FIGS. 50 and 51. At this time, as shown in FIG. 50, if the connected part 132 is engaged with the connecting part 131 at a portion more than half of the outer peripheral of the substantially circular connecting part 131, it is possible to suitably prevent the deviation of the connection of the joint rings 130 in the direction of an axis X1 of the insertion part 102 shown in FIG. 51.

Though in the above embodiment, the one-way clutch 121 provided in the manipulating part 105 is constructed to have the spring 124, instead of this, other known type of a one-way clutch may be employed.

Though in the above embodiment, the fitting part 108 is provided in the first fixing member 107 which is disposed outside the soft member 106, instead of this, a groove of a soft member may be provided in the inner cavity and a fitting part may be provided in the second fixing member 109.

Though the above embodiments employed as an example of the overtube, the structure of the bending part which is formed by connecting the joint rings in the present invention can be employed not only in an overtube but also in other medical instruments which are inserted into the body cavity, such as an endoscope or a procedure instrument.

The invention is not to be considered as being limited by the foregoing description, and is only limited by the scope of the appended claims.

What is claimed is:

1. A medical instrument for performing a medical procedure within a body cavity, the medical instrument comprising:
   an insertion part comprising a bending part capable of bending in a predetermined range;
   a manipulating part which manipulates the bending part; and
   a wire which is arranged to be capable of moving in a longitudinal direction with respect to the insertion part and which connects the bending part with the manipulating part,
   wherein, the manipulating part comprises:
      a handle capable of being rotated and controlled in a predetermined direction to bend the bending part;
      a drive shaft which is connected to the handle at a first end thereof, which is connected to a proximal end of the wire at a second end thereof, and which is capable of rotating by rotation of the handle and by advancing and retreating of the wire;
      a bearing which is substantially-coaxially arranged with respect to the drive shaft to be rotatable and which is fixed to a proximal end of the insertion part; and
      a spring which is engaged to the drive shaft at a first end thereof, which is connected to the handle at a second end thereof, which is formed to be twisted attachably and detachably around both a first outer peripheral surface of the drive shaft and a second outer peripheral surface of the bearing at a predetermined winding diameter thereof, the winding diameter thereof being configured to vary by rotation of the drive shaft,
   wherein:
      the bending part is bent by the wire being pulled by the drive shaft rotating in the predetermined direction in accordance with the rotation of the handle in the predetermined direction,
      a tensile force acting on the wire is generated when the bending part is bent,
      the winding diameter of the spring is decreased by the drive shaft rotating in an opposite direction of the predetermined direction by the tensile force without the handle rotating,
      an inner peripheral surface of the spring comes in contact with both the first outer peripheral surface of the drive shaft and the second outer peripheral surface of the bearing, and both the drive shaft and the bearing are fastened with the spring by the winding diameter of the spring decreasing so that the rotation of the drive shaft is stopped and the drive shaft is connected to the bearing with the drive shaft being incapable of rotating, and the bending part is kept bent by the spring preventing the drive shaft from rotating.

2. The medical instrument according to claim 1, wherein the manipulating part further comprises a pulley which connects the wire with the drive shaft.

3. The medical instrument according to claim 1, wherein the wire connects the bending part with the manipulating part such that the wire is slack when the bending part is straight.

4. The medical instrument according to claim 1, wherein:

the manipulating part further comprises a cover which covers the spring and which is configured to be rotated with the spring, and the first end of the spring is connected to the drive shaft and the second end of the spring is connected to the cover.

\* \* \* \* \*